(12) United States Patent
Fraden et al.

(10) Patent No.: US 10,942,095 B2
(45) Date of Patent: Mar. 9, 2021

(54) MICROFLUIDIC DEVICES FOR INVESTIGATING CRYSTALLIZATION

(71) Applicant: BRANDEIS UNIVERSITY, Waltham, MA (US)

(72) Inventors: Seth Fraden, Newton, MA (US); Michael Heymann, Hamburg (DE); Markus Ludwig, Waltham, MA (US)

(73) Assignee: Brandeis University, Waltham, MA (US)

( * ) Notice: Subject to any disclaimer, the term of this patent is extended or adjusted under 35 U.S.C. 154(b) by 0 days.

(21) Appl. No.: 16/447,369

(22) Filed: Jun. 20, 2019

(65) Prior Publication Data

US 2019/0346347 A1 Nov. 14, 2019

Related U.S. Application Data

(63) Continuation of application No. 15/505,450, filed as application No. PCT/US2015/046465 on Aug. 24, 2015, now Pat. No. 10,365,188.

(Continued)

(51) Int. Cl.
*G01N 1/28* (2006.01)
*B01L 3/00* (2006.01)
(Continued)

(52) U.S. Cl.
CPC .............. *G01N 1/28* (2013.01); *B01D 9/0036* (2013.01); *B01D 9/0072* (2013.01);
(Continued)

(58) Field of Classification Search
CPC ........... C30B 27/00; C30B 29/54; B01D 9/02; C12M 3/00; G01N 1/28
See application file for complete search history.

(56) References Cited

U.S. PATENT DOCUMENTS 8,422,632 B2 * 4/2013 Fowler ............. G01N 23/20025
378/208
2004/0109793 A1 6/2004 McNeely
(Continued)

OTHER PUBLICATIONS

The International Search Report and Written Opinion, dated Jan. 11, 2016, for International Patent Application No. PCT/US2015/046465.

(Continued)

*Primary Examiner* — Robert M Kunemund
(74) *Attorney, Agent, or Firm* — Quarles & Brady LLP

(57) ABSTRACT

Microfluidic devices and methods for investigating crystallization and/or for controlling a reaction or a phase transition are disclosed. In one embodiment, the microfluidic device includes a reservoir layer; a membrane disposed on the reservoir layer; a wetting control layer disposed on the membrane; and a storage layer disposed on the wetting control layer, wherein the wetting control layer and the storage layer define a microfluidic channel comprising an upstream portion, a downstream portion, a first fluid path in communication with the upstream and the downstream portions, and a storage well positioned within the first fluid path, wherein the wetting control layer includes a fluid passageway in communication with the storage well and the membrane, and wherein the wetting control layer wets a first fluid introduced into the microfluidic channel, the first fluid comprising a hydrophilic, lipophilic, fluorophilic or gas phase as the continuous phase in the microfluidic channel.

26 Claims, 17 Drawing Sheets

Related U.S. Application Data

(60) Provisional application No. 62/040,820, filed on Aug. 22, 2014.

(51) Int. Cl.
  *B01D 9/00* (2006.01)
  *G01N 23/20025* (2018.01)
  *C12M 3/00* (2006.01)
  *G01N 1/40* (2006.01)

(52) U.S. Cl.
  CPC ... *B01L 3/502761* (2013.01); *B01L 3/502784* (2013.01); *C12M 3/00* (2013.01); *G01N 23/20025* (2013.01); *B01L 3/502707* (2013.01); *B01L 3/502723* (2013.01); *B01L 2200/025* (2013.01); *B01L 2200/141* (2013.01); *B01L 2300/088* (2013.01); *B01L 2300/0829* (2013.01); *B01L 2300/0887* (2013.01); *B01L 2300/123* (2013.01); *B01L 2300/161* (2013.01); *B01L 2300/1894* (2013.01); *B01L 2400/0487* (2013.01); *B01L 2400/0688* (2013.01); *G01N 2001/4016* (2013.01)

(56) References Cited

U.S. PATENT DOCUMENTS

| | | |
|---|---|---|
| 2004/0115731 A1 | 6/2004 | Hansen |
| 2005/0266582 A1 | 12/2005 | Modlin |
| 2010/0022007 A1* | 1/2010 | Kenis ............... B01F 3/0807 436/8 |
| 2010/0105866 A1 | 4/2010 | Fraden |
| 2011/0155667 A1 | 6/2011 | Charest |
| 2011/0301535 A1 | 12/2011 | Takayama |
| 2012/0018306 A1 | 1/2012 | Srinivasan |
| 2012/0021523 A1* | 1/2012 | Fowler ............ G01N 23/20025 436/4 |
| 2012/0065277 A1 | 3/2012 | Balagadde |
| 2012/0190127 A1 | 7/2012 | Fraden |
| 2013/0101995 A1* | 4/2013 | Rustem ................ C12Q 1/6806 435/6.1 |

OTHER PUBLICATIONS

Kornreich, M. et al., "Cross polarization compatible dialysis chip." Lab on a Chip 1419 (Jul. 2014): 3700-304; abstract; p. 3701, col. 1, 2nd-3rd paragraph; p. 3701, col. 2, 1st, 4th paragraph.

Shim, J.-U., et al. "Using microfluidics to decouple nucleation and growth of protein crystals." Crystal Growth and Design 7.11 (2007): 2192-2194.

* cited by examiner

Single membrane chip
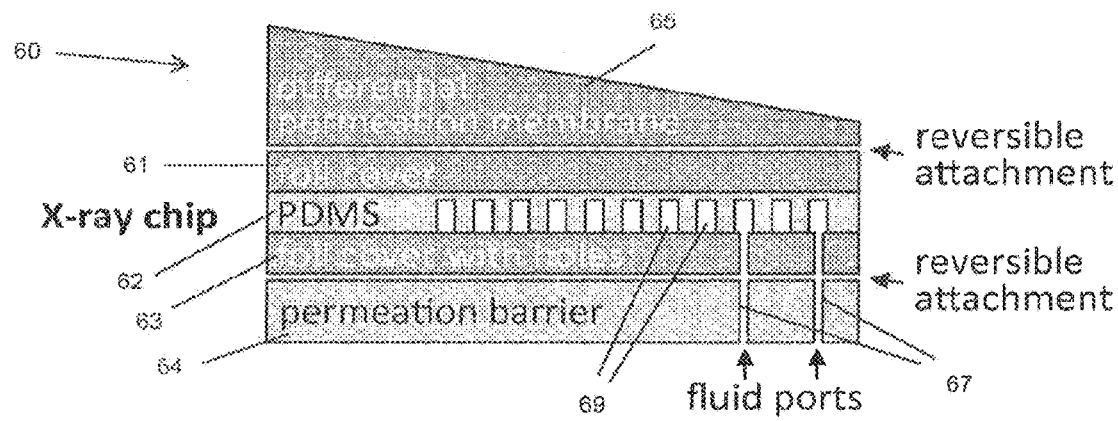
Double membrane chip
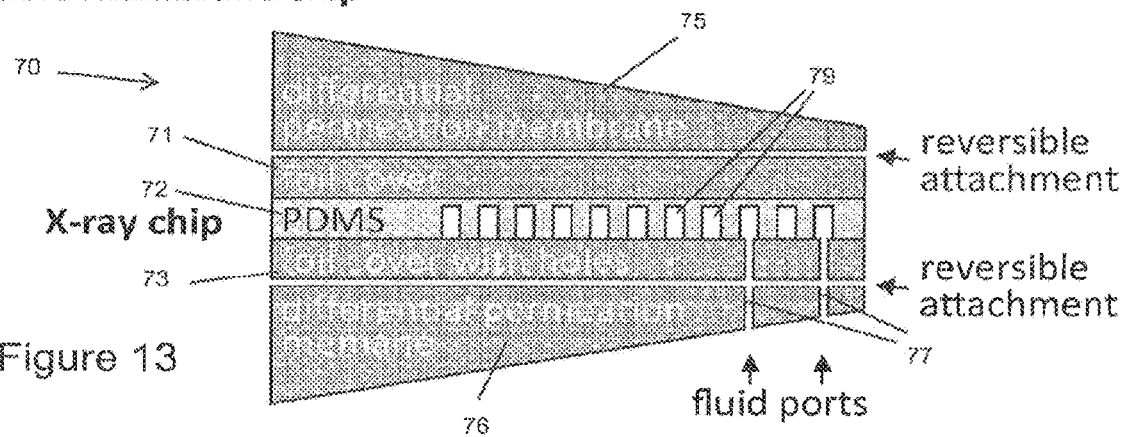
Figure 13

Yeast, 20 nl wells, timelapse ~ 1 week

MICROFLUIDIC DEVICES FOR INVESTIGATING CRYSTALLIZATION

CROSS-REFERENCES TO RELATED APPLICATIONS

This is a continuation application of U.S. patent application Ser. No. 15/505,450 filed Feb. 21, 2017 now U.S. Pat. No. 10,365,188 which is a 371 of PCT International Application No. PCT/US2015/046465 filed on Aug. 24, 2015 which claims priority from U.S. Patent Application No. 62/040,820 filed Aug. 22, 2014.

STATEMENT REGARDING FEDERALLY SPONSORED RESEARCH

This invention was made with government support under 0754769 awarded from the National Science Foundation. The United States government has certain rights in the invention.

BACKGROUND OF THE INVENTION

1. Field of the Invention

This invention relates to microfluidic devices for investigating crystallization.

2. Description of the Related Art

Although protein crystallography can be a very successful technique for structure determination, membrane proteins continue to present challenges to crystallization. It has been reported that two thirds of purified proteins fail to produce diffraction quality protein crystals. Of the human membrane proteins, representing one third of the genome, only a few have had their structure solved using X-ray diffraction. In many cases, the number of crystallization trials is limited by the availability of human protein, which does not express well in bacteria, hence the drive to minimize sample volume.

The paradigm guiding many crystallization efforts is that the conditions for which an equilibrium crystal phase exists are a small subset among a vastly larger set of parameters such as protein concentration, pH, various salts, polymers, temperature, and surfactants. However, it is not widely appreciated that finding the correct equilibrium conditions, while a necessary condition, is not sufficient to produce crystals because crystallization is a non-equilibrium process. Consequently, crystallization methods that focus on screening large number of conditions were often incomplete. Additionally, it may be helpful to optimize the non-equilibrium kinetics of protein crystallization and exploit the crystals that are produced by these methods in order to obtain high quality diffraction data.

Under many previous methods, protein crystals are produced by trial and error, which necessitates exploring a large number of conditions consuming milligrams of protein. Many methods employed in small non-automated labs require about 1 microliter of solution per trial. Automation with expensive robotics has lowered volumes to the 100 nanoliter (nL) range in some instances. Microfluidic devices can reduce the volume per trial to 1 nL or less in many instances. Such small volumes prove useful to screen conditions. However, when crystals are produced in 1 nL drops, they can be less than 30 microns in diameter, which may be too small for current diffraction methods. Scale-up from microfluidic systems also may involve different physics and can be difficult. Even if large crystals are obtained, then they may be required to be cryoprotected, which can damage crystals. Finally the crystals must be aligned in the x-ray beam in many systems.

U.S. Patent Application Publication No. 2012/0190127 to Fraden describes a Crystal Optimizer that is designed to optimize the crystallization kinetics by systematically varying the kinetic supersaturation profile of the crystallization solution. The technology of U.S. 2012/0190127 can be used to crystallize proteins on the salvage pathway (promising crystals that fail to yield structures), including human membrane G-protein-coupled receptors. Given the paucity of crystallized human membrane proteins and the fact that 50% of marketed drugs target G-protein-coupled receptors, the systems and methods of U.S. 2012/0190127 can impact fields such as structural biology and pharmaceutical development.

In the pharmaceutical field, crystal polymorphism can have dramatic differences in biological activity between two forms of the same drug. For example, a metastable polymorph may have higher solubility that leads to an increase in the absorption rate and bioavailability of a drug administered orally. Synthetic and analytic departments of leading pharmaceutical companies carry out systematic work to detect polymorphism of their drugs and to find intelligent applications of this phenomenon. The systems and methods of U.S. 2012/0190127 can benefit such systematic work in detecting polymorphism of drugs.

The Crystal Optimizer of U.S. 2012/0190127 addressed the problem of crystal creation by determining favorable conditions for crystallization using microfluidics. However, there is still a need for further microfluidic technology improvements that allow for a systematic and reversible kinetic control of crystallization trajectory and diffraction studies of crystallized molecules.

SUMMARY OF THE INVENTION

In one aspect, the present invention provides a microfluidic multiplex dialysis chip for mapping phase diagrams with reconfigurable chemical potential.

In another aspect, the present invention provides a technology based on emulsion microfluidics in which drops of protein solution are encapsulated in oil and stabilized by surfactant. We optimize nucleation and growth by generating hundreds of different kinetic paths simultaneously by varying both temperature and concentration of the protein solution. Once the optimal kinetic path is determined, we process an entire emulsion under optimal conditions to generate one crystal per drop. The microfluidic device of this version of the invention can operate with a dialysis membrane, allowing us to optimize kinetic trajectories against various small molecule solutes, such as salts, pH and surfactants. The microfluidic device is compatible for in situ structure studies by X-ray diffraction.

In another aspect, the present invention provides a room temperature serial crystallography method using a kinetically optimized microfluidic device for protein crystallization and on-chip X-ray diffraction. The emulsion based serial crystallographic technology can use nanoliter sized droplets of protein solution encapsulated in oil and stabilized by surfactant. Once the first crystal in a drop is nucleated, the small volume generates a negative feedback mechanism that lowers the supersaturation, which we exploit to produce one crystal per drop. We diffract, one crystal at a time, from a series of room temperature crystals stored on an X-ray semi-transparent microfluidic chip and obtain a complete data set by merging single diffraction frames taken from different unoriented crystals.

In another aspect, the present invention provides devices for supporting crystals in an X-ray diffraction apparatus and methods for making the devices.

In another aspect, the present invention provides kits for making devices for acquiring X-ray diffraction images of one or more crystals.

It is therefore an advantage of the invention to provide improved microfluidic devices for investigating crystallization.

These and other features, aspects, and advantages of the present invention will become better understood upon consideration of the following detailed description, drawings and appended claims.

BRIEF DESCRIPTION OF THE DRAWINGS

FIG. 13 shows cross sectional views of a single membrane differential permeation X-ray chip and a double membrane differential permeation X-ray chip according to the invention.

Like reference numerals will be used to refer to like parts from Figure to Figure in the following description of the drawings.

DETAILED DESCRIPTION OF THE INVENTION

Figure 1:
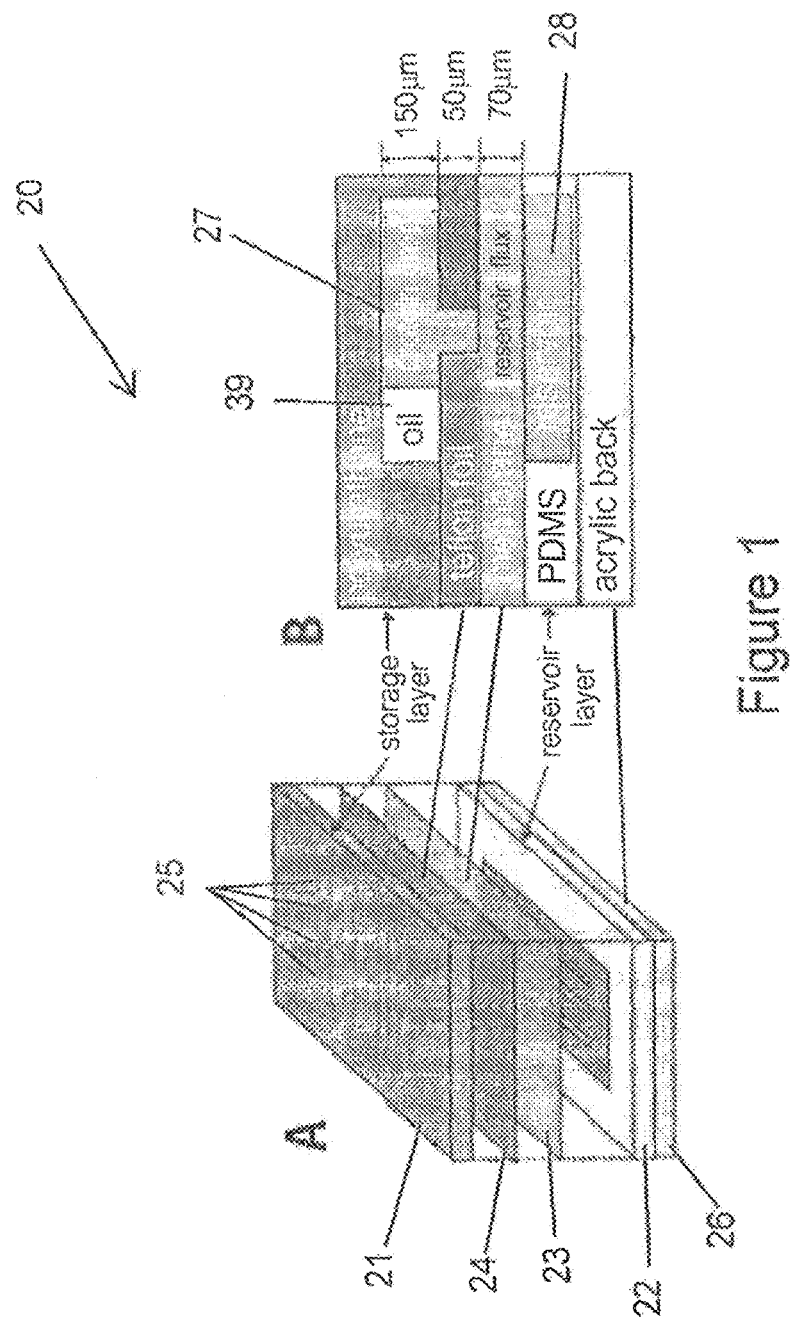
FIG. 1 shows: in (A), a schematic exploded perspective view of one embodiment of a microfluidic dialysis Phase Chip according to the invention, and in (B), a transverse cross-sectional view of a single storage well of the Phase Chip in (A).

In one embodiment, the invention provides a microfluidic device including a reservoir layer defining a reservoir; a membrane disposed on the reservoir layer; a wetting control layer disposed on the membrane; and a storage layer disposed on the wetting control layer. The wetting control layer and the storage layer define a microfluidic channel comprising an upstream portion, a downstream portion, a first fluid path in fluid communication with the upstream portion and the downstream portion, and a storage well positioned within the first fluid path. As used herein, an upstream portion is situated in the opposite direction from that in which the fluid flows, whereas a downstream portion is situated in the direction in which the fluid flows. The wetting control layer includes a fluid passageway in fluid communication with the storage well and the membrane. The wetting control layer is capable of wetting a first fluid introduced into the microfluidic channel, the first fluid comprising a hydrophilic, lipophilic, fluorophilic or gas phase as the continuous phase in the microfluidic channel.

In certain embodiments of the microfluidic device, the membrane comprises a dialysis membrane, or the membrane comprises a membrane permeable to water, or the membrane comprises a polyethersulfone, or the membrane comprises regenerated cellulose or cellulose ester, or the membrane is hydrophilic.

In certain embodiments of the microfluidic device, the wetting control layer comprises a fluoropolymer, and the first fluid comprises a fluorinated oil. The wetting control layer may comprise a polymeric material selected from the group consisting of fluoroakylenes and blends and copolymers thereof. The wetting control layer may comprise fluorinated ethylene propylene. The storage layer may include a fluorophilic coating.

In certain embodiments of the microfluidic device, the reservoir, the membrane, the wetting control layer and the storage layer are reversibly secured together by clamping or are laminated together. The fluid passageway may be aligned with the reservoir.

In certain embodiments of the microfluidic device, a plurality of storage wells are positioned within the first fluid path, the reservoir layer defines a plurality of reservoirs, and each reservoir is aligned with one of the storage wells. The storage layer may comprise polyurethane, and the reservoir layer may comprise polydimethylsiloxane. The storage layer and the reservoir layer may each comprise plastic, fluoroplastic, or glass.

In another embodiment, the invention provides a microfluidic device including a microfluidic channel comprising an upstream portion, a downstream portion, a first fluid path in fluid communication with the upstream portion and the downstream portion, a second fluid path in fluid communication with the upstream portion and the downstream portion. The second fluid path branches from the upstream portion and reconnects at the downstream portion. A well is positioned within the first fluid path, and a plurality of fluid constrictions are in fluid communication with the well and the downstream portion. The first fluid path has less resistance to flow compared to the second fluid path prior to positioning of a first droplet in the well, and the first fluid path has greater resistance to flow compared to the second fluid path after positioning of the first droplet in the well.

In certain embodiments of the microfluidic device, the well has a well height, and each of the fluid constrictions has a constriction height less than the well height. The well may have a well cross-sectional area measured perpendicular to a fluid flow direction in the microfluidic channel greater than a first fluid path cross-sectional area measured perpendicular to the fluid flow direction in the microfluidic channel.

In another embodiment, the invention provides a device for supporting crystals in an X-ray diffraction apparatus. The device includes a first X-ray transparent layer including a microfluidic channel having a microwell positioned therein; a second X-ray transparent layer including a reservoir; and a membrane. The first X-ray transparent layer is attached to a first side of a membrane, and the second X-ray transparent layer is attached to a second opposite side of the membrane such that at least a portion of an opening of the well and at least a portion of an opening of the reservoir are aligned.

In certain embodiments of the device for supporting crystals in an X-ray diffraction apparatus, a plurality of microwells are positioned within the microfluidic channel, the second X-ray transparent layer defines a plurality of reservoirs, and each reservoir is aligned with one of the microwells. The first X-ray transparent layer may comprise an X-ray transparent material selected from the group consisting of cycloolefin polymers, cycloolefin copolymers, polyimides, graphene, and silicon nitride, and the second X-ray transparent layer may comprise the X-ray transparent material. The first X-ray transparent layer may comprise a cycloolefin copolymer, and the second X-ray transparent layer may comprise a cycloolefin copolymer. In one embodiment, the first X-ray transparent layer comprises poly(4,4-oxydiphenylene pyromellitimide), and the second X-ray transparent layer comprises poly(4,4-oxydiphenylene pyromellitimide).

In certain embodiments of the device for supporting crystals in an X-ray diffraction apparatus, the first X-ray transparent layer is less than 200 microns in thickness, and the second X-ray transparent layer is less than 200 microns in thickness. The first X-ray transparent layer may be less than 100 microns in thickness, and the second X-ray transparent layer may be less than 100 microns in thickness. The first X-ray transparent layer may be less than 50 microns in thickness, and the second X-ray transparent layer may be less than 50 microns in thickness. The first X-ray transparent layer may be less than 10 microns in thickness, and the second X-ray transparent layer may be less than 10 microns in thickness.

In certain embodiments of the device for supporting crystals in an X-ray diffraction apparatus, the membrane may comprise a dialysis membrane. The membrane may comprise a membrane permeable to water. The membrane may be hydrophilic. The membrane may be less than 50 microns in thickness.

In another embodiment, the invention provides a method for making a device for supporting crystals in an X-ray diffraction apparatus. The method includes the steps of (a) providing a first mold; (b) using the first mold to emboss a microfluidic channel in a first X-ray transparent layer wherein the microfluidic channel has a microwell positioned therein; (c) providing a second mold; (d) using the second mold to emboss a reservoir in a second X-ray transparent layer; (e) attaching the first X-ray transparent layer to a first side of a membrane; and (f) attaching the second X-ray transparent layer to a second opposite side of the membrane such that at least a portion of an opening of the well and at least a portion of an opening of the reservoir are aligned.

In certain embodiments of the method for making a device for supporting crystals in an X-ray diffraction apparatus, a plurality of microwells are embossed within the microfluidic channel, a plurality of reservoirs are embossed in the second X-ray transparent layer, and each reservoir is aligned with one of the microwells. The first X-ray transparent layer may comprise an X-ray transparent material selected from the group consisting of cycloolefin polymers, cycloolefin copolymers, polyimides, graphene, and silicon nitride, and the second X-ray transparent layer may comprise the X-ray transparent material. The first X-ray transparent layer may comprise a cycloolefin copolymer, and the second X-ray transparent layer may comprise a cycloolefin copolymer. The first X-ray transparent layer may comprise poly(4,4-oxydiphenylene pyromellitimide), and the second X-ray transparent layer may comprise poly(4,4-oxydiphenylene pyromellitimide).

In certain embodiments of the method for making a device for supporting crystals in an X-ray diffraction apparatus, the first X-ray transparent layer is less than 200 microns in thickness, and the second X-ray transparent layer is less than 200 microns in thickness. The first X-ray transparent layer may be less than 100 microns in thickness, and the second X-ray transparent layer may be less than 100 microns in thickness. The first X-ray transparent layer may be less than 50 microns in thickness, and the second X-ray transparent layer may be less than 50 microns in thickness. The first X-ray transparent layer may be less than 10 microns in thickness, and the second X-ray transparent layer may be less than 10 microns in thickness.

In certain embodiments of the method for making a device for supporting crystals in an X-ray diffraction apparatus, the membrane comprises a dialysis membrane. The membrane may comprise a membrane permeable to water. The membrane may be hydrophilic. The membrane may be less than 50 microns in thickness.

In certain embodiments of the method for making a device for supporting crystals in an X-ray diffraction apparatus, the method may include the steps of: (a) introducing a first fluid into the microwell, the first fluid comprising a protein solution; and (b) introducing a second fluid into the reservoir, wherein the first fluid, the second fluid and the membrane are chosen such that a crystal forms in the microwell. The method may include the step of controlling a temperature of the first fluid and the second fluid such that the crystal forms in the microwell.

In another embodiment, the invention provides a device for supporting crystals in an X-ray diffraction apparatus. The device includes a first X-ray transparent layer; a second X-ray transparent layer; and a storage layer including a microfluidic channel having a plurality of microwells positioned therein for containing the crystals. The first X-ray transparent layer is attached to a first side of the storage layer, and the second X-ray transparent layer is attached to a second opposite side of the storage layer.

In certain embodiments of the device for supporting crystals in an X-ray diffraction apparatus, the first X-ray transparent layer comprises an X-ray transparent material selected from the group consisting of cycloolefin polymers, cycloolefin copolymers, polyimides, graphene, and silicon nitride, and the second X-ray transparent layer comprises the X-ray transparent material. The first X-ray transparent layer may comprise a cycloolefin copolymer, and the second X-ray transparent layer may comprise a cycloolefin copolymer. The first X-ray transparent layer may comprise poly(4,4-oxydiphenylene pyromellitimide), and the second X-ray transparent layer may comprise poly(4,4-oxydiphenylene pyromellitimide).

In certain embodiments of the device for supporting crystals in an X-ray diffraction apparatus, the first X-ray transparent layer is less than 200 microns in thickness, and the second X-ray transparent layer is less than 200 microns in thickness. The first X-ray transparent layer may be less than 100 microns in thickness, and the second X-ray transparent layer may be less than 100 microns in thickness. The first X-ray transparent layer may be less than 50 microns in thickness, and the second X-ray transparent layer may be less than 50 microns in thickness. The first X-ray transparent layer may be less than 10 microns in thickness, and the second X-ray transparent layer may be less than 10 microns in thickness.

In another embodiment, the invention provides a method for making a device for supporting crystals in an X-ray diffraction apparatus. The method includes the steps of (a) providing a master mold; (b) using the master mold to form a storage layer including a microfluidic channel having a plurality of microwells; (c) attaching a first X-ray transparent layer to a first side of the storage layer; and (d) attaching a second X-ray transparent layer to a second opposite side of the storage layer. The method may include the step of introducing a first fluid into the microwells, wherein the first fluid comprises a protein solution or a protein crystal.

In certain embodiments of the method for making a device for supporting crystals in an X-ray diffraction apparatus, the first X-ray transparent layer comprises an X-ray transparent material selected from the group consisting of cycloolefin polymers, cycloolefin copolymers, polyimides, graphene, and silicon nitride, and the second X-ray transparent layer comprises the X-ray transparent material. The first X-ray transparent layer may comprise a cycloolefin copolymer, and the second X-ray transparent layer may comprise a cycloolefin copolymer. The first X-ray transparent layer may comprise poly(4,4-oxydiphenylene pyromellitimide), and the second X-ray transparent layer may comprise poly(4,4-oxydiphenylene pyromellitimide).

In certain embodiments of the method for making a device for supporting crystals in an X-ray diffraction apparatus, the first X-ray transparent layer is less than 200 microns in thickness, and the second X-ray transparent layer is less than 200 microns in thickness. The first X-ray transparent layer may be less than 100 microns in thickness, and the second X-ray transparent layer may be less than 100 microns in thickness. The first X-ray transparent layer may be less than 50 microns in thickness, and the second X-ray transparent layer may be less than 50 microns in thickness. The first X-ray transparent layer may be less than 10 microns in thickness, and the second X-ray transparent layer may be less than 10 microns in thickness.

In another embodiment, the invention provides a device for supporting crystals in an X-ray diffraction apparatus. The device includes an X-ray transparent layer; and a storage section in the X-ray transparent layer, wherein the X-ray transparent layer and a first side of the storage section define a microfluidic channel having a plurality of microwells positioned therein for containing the crystals.

In certain embodiments of the device for supporting crystals in an X-ray diffraction apparatus, the X-ray transparent layer comprises an X-ray transparent material selected from the group consisting of cycloolefin polymers, cycloolefin copolymers, polyimides, graphene, and silicon nitride. The X-ray transparent layer may comprise a cycloolefin copolymer. The X-ray transparent layer may comprise poly(4,4-oxydiphenylene pyromellitimide). The X-ray transparent layer may be less than 200 microns in thickness. The X-ray transparent layer may be less than 100 microns in thickness. The X-ray transparent layer may be less than 50 microns in thickness. The X-ray transparent layer may be less than 10 microns in thickness.

In certain embodiments of the device for supporting crystals in an X-ray diffraction apparatus, the microfluidic channel is formed in the storage section. The device may include a single X-ray transparent layer.

In another embodiment, the invention provides a kit for acquiring X-ray diffraction images of one or more crystals. The kit includes any of the devices for supporting crystals in an X-ray diffraction apparatus as described above. The kit further includes a crystallization trial device comprising: (i) a reservoir layer defining a plurality of reservoirs, (ii) a storage layer defining a microfluidic channel having a plurality of microwells positioned therein, and (iii) a membrane positioned between the reservoir layer and the storage layer, wherein at least a portion of an opening of each microwell is aligned with an opening of a reservoir of the reservoir layer.

In another embodiment, the invention provides a kit for acquiring X-ray diffraction images of one or more crystals. The kit includes a first X-ray transparent layer including a microfluidic channel having a plurality of microwells; a second X-ray transparent layer including one or more reservoirs; a membrane; and a fastening system for attaching the first X-ray transparent layer to a first side of the membrane and for attaching the second X-ray transparent layer to a second opposite side of the membrane.

In certain embodiments of the kit for acquiring X-ray diffraction images of one or more crystals, the first X-ray transparent layer and the second X-ray transparent layer are structured such that at least a portion of an opening of each microwell can be aligned with an opening of a reservoir in the second X-ray transparent layer. The first X-ray transparent layer may be less than 100 microns in thickness, and the second X-ray transparent layer may be less than 100 microns in thickness. The first X-ray transparent layer may comprise an X-ray transparent material selected from the group consisting of cycloolefin polymers, cycloolefin copolymers, polyimides, graphene, and silicon nitride, and the second X-ray transparent layer may comprise the X-ray transparent material. The membrane may comprise a dialysis membrane.

The kit may include a crystallization trial device comprising: (i) a reservoir layer defining a plurality of reservoirs, (ii) a storage layer defining a microfluidic channel having a plurality of microwells positioned therein, and (iii) a membrane positioned between the reservoir layer and the storage layer, wherein at least a portion of an opening of each microwell is aligned with an opening of a reservoir of the reservoir layer.

In another embodiment, the invention provides a kit for acquiring X-ray diffraction images of one or more crystals. The kit includes a supply of X-ray transparent material; a first mold for embossing a microfluidic channel having a plurality of microwells in a first section of the X-ray transparent material so as to create a first X-ray transparent layer; a second mold for embossing one or more reservoirs in a second section of the X-ray transparent material so as to create a second X-ray transparent layer; a membrane; and a fastening system for attaching the first X-ray transparent layer to a first side of the membrane and for attaching the second X-ray transparent layer to a second opposite side of the membrane.

In certain embodiments of the kit for acquiring X-ray diffraction images of one or more crystals, the first mold and the second mold are structured such that at least a portion of an opening of each microwell is aligned with an opening of a reservoir in the second X-ray transparent layer. The X-ray transparent material may be less than 100 microns in thickness. The X-ray transparent material may comprise a material selected from the group consisting of cycloolefin polymers, cycloolefin copolymers, polyimides, graphene, and silicon nitride. The membrane may comprise a dialysis membrane.

The kit may include a crystallization trial device comprising: (i) a reservoir layer defining a plurality of reservoirs, (ii) a storage layer defining a microfluidic channel having a plurality of microwells positioned therein, and (iii) a membrane positioned between the reservoir layer and the storage layer, wherein at least a portion of an opening of each microwell is aligned with an opening of a reservoir of the reservoir layer.

In another embodiment, the invention provides a method for acquiring X-ray diffraction images of crystals. The method includes the steps of: (a) micro-fluidically producing droplets; (b) feeding the droplets into a microfluidic channel of an X-ray device wherein the microfluidic channel has a plurality of microwells positioned therein for containing the droplets, and the X-ray device is at least partially X-ray transparent; (c) nucleating and growing a crystal in least some of the droplets to create a plurality of crystals; and (d) obtaining an X-ray diffraction pattern from the plurality of crystals.

In certain embodiments of the method for acquiring X-ray diffraction images of crystals, the X-ray device comprises an X-ray transparent layer attached to a first side of a storage layer, the X-ray transparent layer and the first side of the storage layer defining the microfluidic channel. The X-ray device may comprise a first X-ray transparent layer, a second X-ray transparent layer, and a storage layer including the microfluidic channel, wherein the first X-ray transparent layer is attached to a first side of the storage layer, and the second X-ray transparent layer is attached to a second opposite side of the storage layer. The droplets may be monodisperse. The droplets may have a size such that a single crystal is grown in each droplet. Each crystal may grow by permeation of water in the X-ray device. Each crystal may grow by dialysis in the X-ray device. Preferably, the method does not include a cryoprotection step.

In another embodiment, the invention provides a device for growing crystals. The device includes a storage layer having a plurality of microwells positioned therein for containing the crystals; a first X-ray transparent layer attached to a first side of the storage layer; a second X-ray transparent layer is attached to a second opposite side of the storage layer; and a differential permeation membrane attached to the first X-ray transparent layer.

In certain embodiments of the device for growing crystals, the first X-ray transparent layer comprises an X-ray transparent material selected from the group consisting of cycloolefin polymers, cycloolefin copolymers, polyimides, graphene, and silicon nitride, and the second X-ray transparent layer comprises the X-ray transparent material. The first X-ray transparent layer may comprise a cycloolefin copolymer, and the second X-ray transparent layer may comprise a cycloolefin copolymer. The first X-ray transparent layer may be less than 200 microns in thickness, and the second X-ray transparent layer may be less than 200 microns in thickness. The first X-ray transparent layer may be less than 100 microns in thickness, and the second X-ray transparent layer may be less than 100 microns in thickness. The first X-ray transparent layer may be less than 50 microns in thickness, and the second X-ray transparent layer may be less than 50 microns in thickness. The first X-ray transparent layer may be less than 10 microns in thickness, and the second X-ray transparent layer may be less than 10 microns in thickness.

In certain embodiments of the device for growing crystals, the differential permeation membrane may be removably attached to the first X-ray transparent layer. The differential permeation membrane may have a thickness that varies from a first end of the differential permeation membrane to an opposite second end of the differential permeation membrane. The differential permeation membrane may be wedge-shaped in cross-section. The device may comprise a second differential permeation membrane attached to the second X-ray transparent layer. The second differential permeation membrane may be removably attached to the second X-ray transparent layer. The second differential permeation membrane may have a thickness that varies from a first end of the second differential permeation membrane to an opposite second end of the second differential permeation membrane. The second differential permeation membrane may be wedge-shaped in cross-section.

In certain embodiments of the device for growing crystals, a permeation barrier is attached to the second X-ray transparent layer. At least one fluid port may be in fluid communication with the plurality of microwells. Each fluid port may be in the second X-ray transparent layer.

In another embodiment, the invention provides a device for containing crystals. The device comprises a chip and a vial dimensioned to receive the chip. The chip includes (i) a storage layer including a plurality of microwells positioned therein for containing the crystals, (ii) a first X-ray transparent layer attached to a first side of the storage layer, and (iii) a second X-ray transparent layer is attached to a second opposite side of the storage layer.

In certain embodiments of the device for containing crystals, the device comprises an aqueous fluid contained in the vial, wherein the aqueous fluid covers the chip when the chip is received in the vial. A seal may cover the aqueous fluid. A source of oil may be contained in the vial, and the source of oil may cover the seal. A conduit may be in fluid communication with the source of oil and the storage layer. The vial may have an opening such that hydrostatic pressure can push oil into the storage layer to replace oil that has evaporated. The first X-ray transparent layer and the second X-ray transparent layer may each be less than 100 microns in thickness. The first X-ray transparent layer and the second X-ray transparent layer may each be less than 10 microns in thickness.

In another embodiment, the invention provides an apparatus for controlling a reaction or a phase transition. The apparatus includes a microfluidic device having a reservoir layer defining a reservoir; a dialysis membrane disposed on the reservoir layer; a wetting control layer disposed on the membrane; and a storage layer disposed on the wetting control layer. The wetting control layer and the storage layer define a microfluidic channel comprising a storage well. The wetting control layer includes a fluid passageway in fluid communication with the storage well and the membrane. The wetting control layer is capable of wetting a first fluid introduced into the microfluidic channel, the first fluid comprising a hydrophilic, lipophilic, fluorophilic or gas phase as the continuous phase in the microfluidic channel. The apparatus further includes: a source of oil in fluid communication with the storage well of the microfluidic channel of the microfluidic device; and a source of an aqueous fluid (e.g., a buffer) in fluid communication with the reservoir of the microfluidic device. Hydrostatic pressure regulates transport fluxes across the membrane.

In certain embodiments of the apparatus for controlling a reaction or a phase transition, the membrane is a dialysis membrane. In the apparatus, hydrostatic pressure may regulate transport fluxes across the membrane. A pressure controller may regulate transport fluxes across the membrane. The aqueous fluid may be a buffer. In the apparatus, outlets of the microfluidic channel may be blocked. An outlet of the reservoir may be open. The apparatus may comprise a microscope for monitoring the reaction or the phase transition in the device. The reaction may be one or more of the following: steady-state and self-assembly reactions at or far from equilibrium; perturbation analysis of reaction networks; cell synchronization; cell and tissue differentiation; and/or chemostat reactions with cells and cell populations. The phase transition may be one or more of the following: crystallization and co-crystallization of small molecules, biological macromolecules, colloids and combinations thereof; liquid crystal phase transitions; gelation; liquid-liquid separation; protein folding; and/or DNA melting or condensation. The reaction may be a chemostat reaction with cells.

In another embodiment, the invention provides an apparatus for controlling a reaction or a phase transition. The apparatus includes a microfluidic device including a microfluidic channel comprising an upstream portion, a downstream portion, a first fluid path in fluid communication with the upstream portion and the downstream portion, a second fluid path in fluid communication with the upstream portion and the downstream portion. The second fluid path branches from the upstream portion and reconnects at the downstream portion. A well is positioned within the first fluid path, and a plurality of fluid constrictions are in fluid communication with the well and the downstream portion. The first fluid path has less resistance to flow compared to the second fluid path prior to positioning of a first droplet in the well, and the first fluid path has greater resistance to flow compared to the second fluid path after positioning of the first droplet in the well. In certain embodiments of the microfluidic device, the well has a well height, and each of the fluid constrictions has a constriction height less than the well height. The well may have a well cross-sectional area measured perpendicular to a fluid flow direction in the microfluidic channel greater than a first fluid path cross-sectional area measured perpendicular to the fluid flow direction in the microfluidic channel.

The reaction may be one or more of the following: steady-state and self-assembly reactions at or far from equilibrium; perturbation analysis of reaction networks; cell synchronization; cell and tissue differentiation; and/or chemostat reactions with cells and cell populations. The phase transition may be one or more of the following: crystallization and co-crystallization of small molecules, biological macromolecules, colloids and combinations thereof; liquid crystal phase transitions; gelation; liquid-liquid separation; protein folding; and/or DNA melting or condensation. The reaction may be a chemostat reaction with cells.

Within this specification, embodiments have been described in a way which enables a clear and concise specification to be written, but it is intended and will be appreciated that embodiments may be variously combined or separated without parting from the invention. For example, it will be appreciated that all features described herein are applicable to all aspects of the invention described herein.

EXAMPLES

The following Examples are provided in order to demonstrate and further illustrate certain embodiments and aspects of the present invention and are not to be construed as limiting the scope of the invention.

Example 1

In this example, we demonstrate a microfluidic multiplex dialysis chip for mapping phase diagrams with reconfigurable chemical potential.

Overview

The Phase Chip described in Shim et al., "Using Microfluidics to Decouple Nucleation and Growth of Protein Crystals", *Crystal Growth & Design* 2007, Vol. 7, No. 11, pages 2192-2194, compartmentalizes protein crystallization trials into nanoliter sized emulsion droplets and can screen up to several thousand kinetic crystallization pathways in parallel, while consuming nanoliter, or even picoliter amounts per sample well. In this example, we introduce a new Phase Chip design that utilizes a dialysis membrane, which greatly extends the range of applications, as any solute smaller than the molecular weight cut-off of the membrane can be dialyzed into and out of the sample wells. The chip is operated by controlling osmotic and hydrostatic pressure to regulate transport fluxes across the membrane. Because of its modular design, the chip can be reused multiple times and also harvest crystals from the chip for structure determination by x-ray diffraction.

INTRODUCTION

Microfluidic technology allows for exceptional control of solution conditions in space and time, which has been exploited to map phase diagrams. In particular, crystallization in microfluidic devices has been investigated. In all these microfluidic approaches to crystallization and in particular with respect to protein crystallization however, it was neglected that crystal nucleation and crystal growth require opposing degrees of supersaturation. To decouple nucleation and growth by means of controlling the chemical potential in the crystallization trial, a Phase Chip as described in Shim et al. has been developed. While the Phase Chip technology of Shim et al. has successfully been demonstrated, its permeation design is limited in certain ways. In the Shim et al. device, the storage layer and the gradient layer are built from separate PDMS pieces, which are covalently bonded together. Thus, chips are single use only. Because chemical coupling takes place across a PDMS membrane in the Shim et al. device, the flux between storage and gradient layer is limited. Small non-polar molecules permeate quickly, but water permeates very slowly and charged molecules do not permeate at experimentally relevant timescales. These poor transport characteristics favor very thin PDMS membranes that are very fragile and often rupture causing failure of the chip. To overcome these limitations, we replaced the PDMS membrane with a regenerated cellulose dialysis membrane (see FIG. 1). Here solute exchange is limited only by the molecular cut-off level of the chosen membrane, and ions, acids, bases or bigger molecules such as pH-buffers or even polymers can diffuse across the membrane. The dialysis Phase Chip 20 of FIG. 1 comprises two microfluidic layers 21, 22 that are separated by a semipermeable dialysis membrane 23 and a perforated Teflon® polytetrafluoroethylene foil 24 for wetting control. The storage layer 21 on top is a matrix of a few hundred and up to a few thousand storage wells 25 that each can hold an isolated protein solution sample. The sample droplets 27 can interact osmotically through the dialysis membrane 23 with the solution perfused in the PDMS reservoir layer 22 located at the bottom of the chip. Water and solutes can exchange between sample droplet and reservoir 28 across the membrane.

Because of the continuous standing column of water in a dialysis membrane, pressure gradients across the membrane can equilibrate through reverse osmosis. This makes it difficult to dialyze nanoliter volumes in parallel. In the microfluidic device of this example, we can exploit osmosis and reverse osmosis to continuously and reversibly reformulate each crystallization cocktail. We can also decouple protein crystal nucleation and growth, by first quenching into a deep supersaturation and then quench back to a low supersaturation. In one non-limiting example embodiment, the chip is a clamped assembly, where the storage layer 21 is made from polyurethane and the reservoir layer 22 from PDMS. The flexible PDMS reservoir is mechanically supported by an acrylic (e.g., poly(methyl methacrylate)) bottom piece 26 to provide a good seal. Because of this modular design where both layers 21, 22 are clamped together, rather than covalently combined, chips can be reused multiple times. However, it is also contemplated that the storage layer 21 and the reservoir layer 22 can be all be fabricated from plastics, fluoroplastics, and/or glass.

Device Fabrication and Assembly

Figure 2:
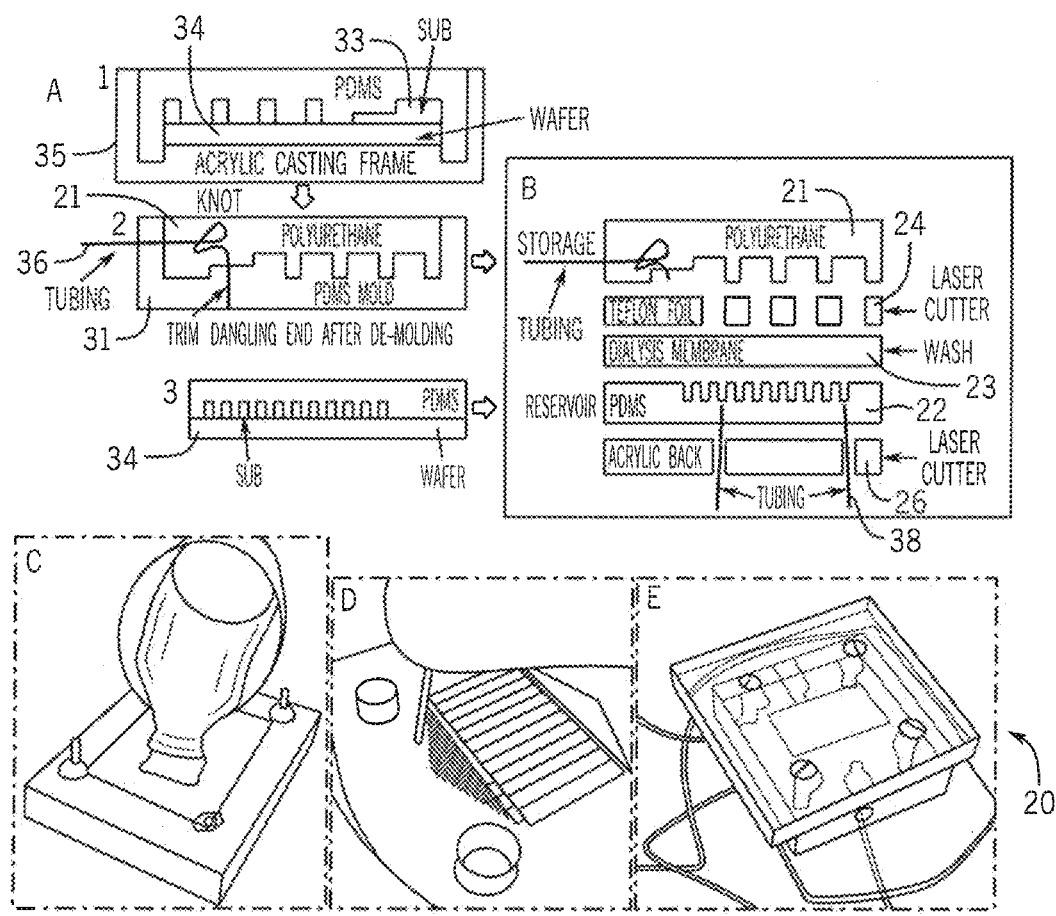
FIG. 2 shows a transverse schematic overview of fabrication workflow (A1-A3) for the Phase Chip of FIG. 1, with an exploded transverse view of the final assembly (B) highlighted in the bounding box. Preparation of a poly (dimethylsiloxane) (PDMS) mold is shown in (C). Insertion of tubing directly into the PDMS reservoir is shown in (D). In (E), a top view of final chip assembled with four screws is shown.

The dialysis Phase Chip of this example was built by combining soft-lithography and replica molding with custom laser cut parts. FIG. 2 shows a schematic overview of fabrication workflow (A1-A3) for the dialysis Phase Chip with the final assembly (B) highlighted in the bounding box. In the first step, we prepared a PDMS mold 31 (A1 and C) so that we could later cast the polyurethane storage layer 21 (A2). We directly casted the tubing for interfacing with the storage layer into the polyurethane. The dangling end was trimmed later. The reservoir was directly molded from a SU8 master (A3). Here we inserted tubing 36 directly into the PDMS reservoir (D) and wound the tubing through the acrylic back. In (E), a top view of final chip 20 assembled with four screws is shown. Scale bars are 1 cm.

Specifically, for fabricating the storage layer, we manufactured an 'inverse' negative resist master where the features are wells surrounded by higher SU8 resist 33. We mounted this wafer 34 into an acrylic casting frame 35 (see FIGS. 2 A1 and C) to cast a PDMS replica that can act as a mold for the polyurethane resin (Crystal Clear 204, Smooth-On, Inc.), which after curing formed the storage layer lid 21. For easy chip-to-world interfacing, we inserted 300 µm inner diameter polyether ether ketone tubing 36 (PEEK tubing, from Cole Parmer) into the PDMS mold, so that it became embedded into the polyurethane piece (see FIG. 2, A2). For this we punched through holes into the PDMS mold using a 0.75 mm biopsy punch (Uni Core, Harrison) and inserted the tubing 36 into these holes to seal off and prevent resin from flowing into the tubing. A small knot in the tubing 36 helped to firmly embed it into the storage lid 21. The PDMS mold was then degassed in a desiccator for 30 minutes, before the polyurethane resin was cast into the mold. We then further degassed until all air-bubbles trapped in the resin had moved to the surface. Usually this was after about 1 hour. We then opened the desiccator and gently popped remaining bubbles using a Pasteur pipette, or a stream of compressed air. We let the polyurethane cure in the oven at 80° C. overnight. After removing the cured polyurethane top from the cast, we drilled through holes and trimmed the dangling end of the tubing. After a quick clean of the device with compressed air, we plasma activated the polyurethane at 500 mTorr (±50 mTorr) 02 plasma at 60 watt for 1 minute, before dip-coating the lid in a 1:50 dilution of Cytop 109 AE in CTsolv 100E (both Bellex International). Cytop is a fluorophilic coating that prevents protein unfolding on the channel surface. To fully cross-link the Cytop to the polyurethane surface, we incubated the lid in the oven at 100° C. over night.

The wetting control layer 24 was cut from a 50 µm thick fluorinated ethylene propylene (FEP) foil (McMaster Carr) using a VLS3.50 Versa laser cutter with 50 watt Imaging Cartridge with High Power Density Focusing Optics (HPDFO). (FIG. 2(B) shows an alternative Teflon® foil for the wetting control layer.)

The PDMS reservoir 22 was cast on a traditional SU8 master, where features built up as posts defined the channels in the PDMS piece (see FIG. 2 A2). To interface into the PDMS reservoir, we punched through-holes using a 0.75 mm biopsy punch (Uni Core, Harrison) and directly inserted the tubing into the holes (see FIG. 2 B). The 73 µm flat sheet regenerated cellulose dialysis membrane with 6000 molecular weight cut-off (Bel-Art Products, Peaquannock, N.J.) was incubated for 15 minutes in ultrafiltered water (Millipore Elix 3) to wash away glycerol and other additives used for storing the membrane. We then washed again for 15 minutes in 10 mM EDTA to remove residual metal ions.

The acrylic back 26 was cut to shape using a VLS3.50 Versa laser cutter with 50 watt Imaging Cartridge with HPDFO and then manually threaded so that four screws could pull the chip-sandwich together.

To assemble the chip (see FIG. 2 E), we positioned the interfaced PDMS reservoir layer 22 on the acrylic back 26. The rinsed dialysis membrane 23 of desired pore-size was then gently dried using Kimwipe tissues such that the membrane was moist inside, but no water puddles remained on its surface. We dispensed 100 µl FC-43 (Sigma Aldrich) onto the dialysis membrane before depositing the wetting control layer 24 on top. Another 100 µl FC-43 were dispensed onto the FEP foil 24 before placing the polyurethane storage layer 21 on top. The FC-43 oil lubricated the FEP foil, so that it could be easily aligned later. We inserted the screws to clamp the sandwich together, aligned the wetting control layer 24 with the polyurethane storage lid 21 and finally tightened the screws until the features in the PDMS reservoir layer 22 were barely beginning to distort from the pressure. We finally primed the chip by dead-end filling via tubing 38 the aqueous reservoir solution into the reservoir 28 and 12 wt % Fluorooctanol in FC-43 39 into the storage layer 21 until no air-bubbles remained trapped in the chip. After each use, all components were washed in a sonicator bath with 1 vol % Helmanex and 1 wt % Zonyle FSN-100 fluorosurfactant for 15 minutes, then repeatedly rinsed with ultrafiltered water, dried with compressed air and stored away for reuse.

Loss-Free Sample Loading Using Capillary Valving

We stored the sample in cylindrical wells. All storage wells were connected in series by a continuous serpentine channel through which one well was loaded after the other (see FIG. 3). To eliminate sample loss from channel dead-volume, we exploited the capillary valve based "store-then-create" loading technique. In brief, the chip was primed with a fluorinated oil before the aqueous sample was injected into the device. The surface tension at the oil-water interface between priming oil and aqueous sample resulted in a pressure difference across the interface. This Laplace pressure can be calculated by the Young-Laplace equation as $$\Delta P = \in \left( \frac{1}{Rx} + \frac{1}{Ry} \right)$$

with $R_x$ and $R_y$ as the main radii of curvature and $\in$ being the surface tension of the interface. To minimize its energy, the interface has to minimize its surface which is equivalent to maximizing its main radii of curvature at constant volume. A low curvature interface in a wide channel has a lower Laplace pressure then a high curvature interface in a narrow channel segment. Therefore, the sample plug preferentially entered and flowed through the wide bypass channel instead of flowing through the narrow capillary valve channel (see FIG. 3). The sample plug was then followed again by oil, which separated the sample in the wells into independent droplets.

Figure 3:
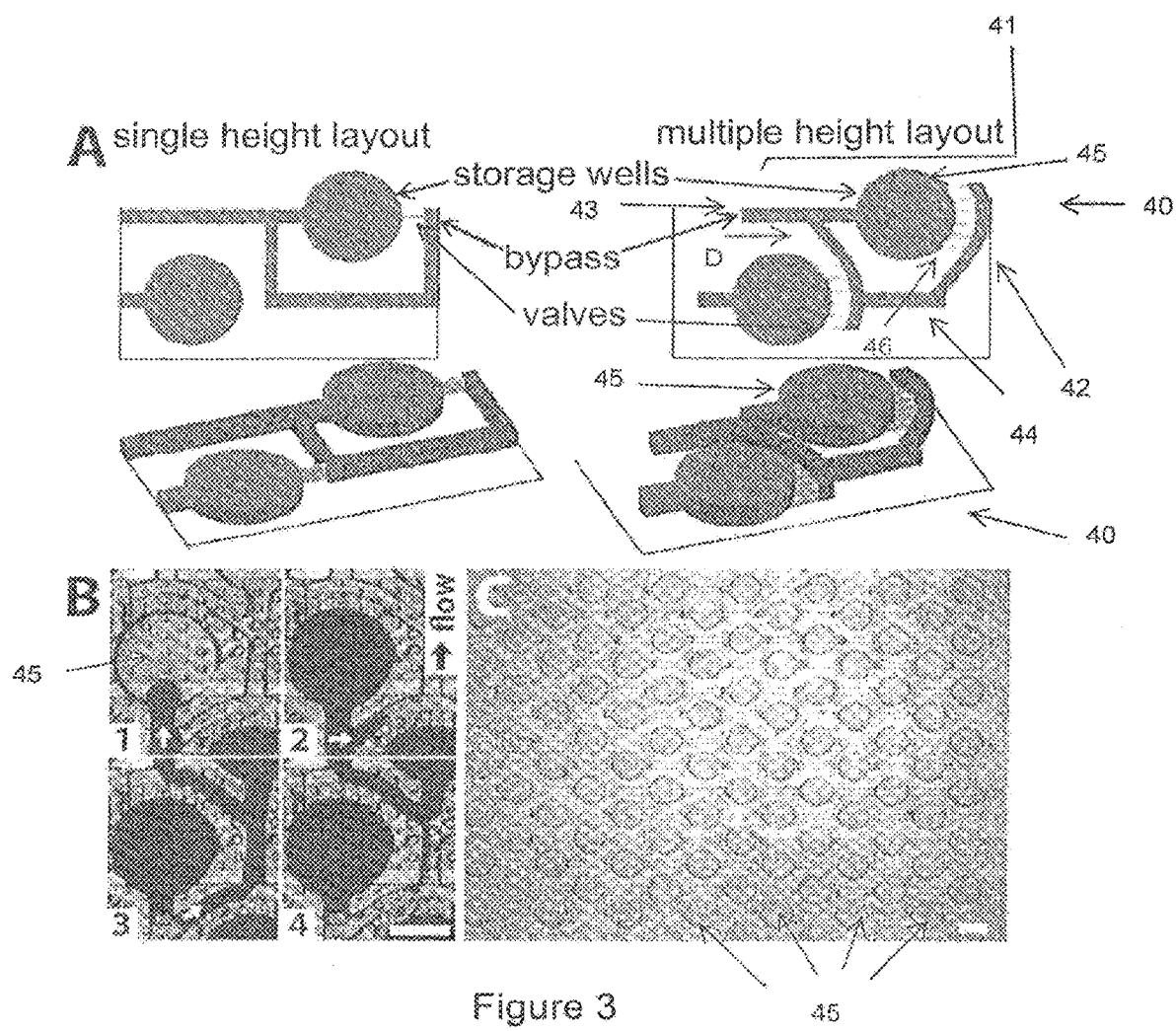
FIG. 3 shows in (A), top plan view and perspective view schematics of an alternative embodiment of a Phase Chip according to the invention with storage layers for the single height design (left) and the multiple height multi-valve design (right), as viewed from top and from the side perspective view. In (B), there is shown a top view image sequence of an aqueous solution of food dye loaded into the storage layer. Channel cross-sections (height·width) of the device used here are bypass=100 μm·100 μm, storage well entry=150 μm·100 μm, and valves=25 μm·80 μm. The chip was primed with 12 wt % Fluoro-octanol in FC-43, before blue food dye was injected into the storage wells. The flow rate was 150 μL/hr throughout the experiment. White arrows indicate the direction of flow. Scale bar=300 μm. In (C), there is shown, a top view of loaded device with all visible 98 wells loaded defect free, illustrating robust sample loading. Scale bar=500 μm.

Compared with the previous design of Shim et al., we improved the Phase Chip storage layout in several ways (see FIG. 3 A). First, we routed the bypass closer around the wells to condense the design. By this we increased the well density by 27%. Second, we made the chip manufacturing more robust by replacing the fragile thin and tall valve in the single height design with a shallow and wide valve in a multi height design. This greatly improves master durability and also allowed us to cast plastic chips from silicone rubber molds. Third, we improved loading efficiency by introducing multiple parallel valves. This, in analogy to electric resistors connected in parallel, reduced the hydrodynamic resistance of the valve section and allowed us to load the chip reliably with flow rates of up to 150 µl/hr, which was a more than a 3 fold increase over the single valve design.

Looking at FIG. 3, a microfluidic channel 40 includes an upstream portion 41, a downstream portion 42, a first fluid path 43 in fluid communication with the upstream portion 41 and the downstream portion 42, a second fluid path 44 in fluid communication with the upstream portion 41 and the downstream portion 42. The second fluid path 44 branches from the upstream portion 41 and reconnects at the downstream portion 42. A well 45 is positioned within the first fluid path, and a plurality of fluid constrictions (valves) 46 are in fluid communication with the well 45 and the downstream portion 42. The first fluid path has less resistance to flow compared to the second fluid path prior to positioning of a first droplet in the well 45, and the first fluid path has greater resistance to flow compared to the second fluid path after positioning of the first droplet in the well 45. The well 45 has a well height, and each of the fluid constrictions 46 has a constriction height less than the well height. The height of each of the fluid constrictions 46 may be the same or different from the other fluid constrictions 46. The well 45 may have a well cross-sectional area measured perpendicular to a fluid flow direction D in the microfluidic channel greater than a first fluid path cross-sectional area measured perpendicular to the fluid flow direction D in the microfluidic channel 40. The first fluid path 43, the second fluid path 44, the well 45, and the plurality of fluid constrictions (valves) 46 may be arrayed in a repeating symmetrical manner as shown in FIGS. 3 B and 3 C.

Assessing Crystal Quality

Crystal nucleation is a non-equilibrium, dynamic process and timely detection of crystal nuclei allows prompt optimization of crystallization recipes. To finely titrate our dialysis crystallization trials into the crystallization zone, we needed to be able to detect the smallest possible nuclei, or ideally even sub-critical nuclei, which have not yet grown larger than the critical size associated with the nucleation barrier. To identify quench profiles that yield a crystalline phase instead of a kinetically arrested gel, we used Second Harmonic Generation imaging. Crystals grown in the chip were then harvested to collect X-ray diffraction data.

SHG Imaging

Second Harmonic Generation (SHG) is the emission of radiated, coherent light at exactly twice the frequency of the incident light. Non-centrosymmetric molecular polarizability can lead to SHG and thus any chiral protein crystal can give a SHG signal, while disordered or centrosymmetric packings of the same individual proteins cannot. These different susceptibilities, make it a powerful detection technique for protein crystals, as even microcrystals can be selectively imaged against a background of solvated protein or amorphous protein aggregates. Exploiting the ratio of the forward-to-backward detected SHG, one can detect sizes of green fluorescent protein microcrystallites and derive a general theoretical detection limit for protein crystallites of down to 100 nanometers in diameter under low magnification with 10× objective. These are detection limits not rivaled by traditional fluorescent, or polarization microscopy methods. Also, usually protein aggregates in solution produce substantial background fluorescence, but no detectable SHG. Similarly, salt crystals are birefringent too, but do not show SHG.

SHG is a scattering process, so there is no bleaching and because it is a 2-photon effect, there is no background SHG. The SHG signal from a protein arises primarily from the amide transition of amino acid residues. Summing the individual hyperpolarizability terms over all residues yields the SHG susceptibility tensor of a single protein. From the SHG susceptibility of a single protein, the SHG signal from a protein cluster can be calculated.

Glucose isomerase crystallizes with orthorhombic symmetry in the space group I222. It is known to have a good SHG signal. We grew crystals by loading 30 mg/ml glucose isomerase at 20 wt % PEG 10000, 100 mM ammonium sulfate, pH 7.3 and subsequently quenching the whole microfluidic chip of this example to 30 wt % PEG 10000, 100 mM ammonium sulfate, pH 7.3. We then sealed all outlets and incubated the chip in a water bath at 4° C. for several days. Crystals were observed inside the chip using bright field microscopy and SHG imaging, using the SON ICC imaging platform (Formulatrix, Waltham, Mass., USA) with 10× objective. Glucose isomerase crystals gave strong SHG signal, while no SHG signal was observed from amorphous aggregation found in a few wells. We did not detect significant background from the chip in SHG. We concluded that the chip with its different components is well suited for SHG imaging.

Harvesting Crystals for X-Ray Crystallography

To mount crystals for cryo crystallography, we carefully opened the chip of this example, by gently pressing the lid down while removing all four screws. We then took the storage lid 21 off the chip and applied 1 ml 40 wt % PEG 10000, 100 mM ammonium sulfate, pH 7.3 onto the lid and also onto the polytetrafluoroethylene foil 24 and dialysis membrane 23 left behind on top of the reservoir layer 22, as crystals stayed on both halves. The 40 wt % PEG buffer was used as a cryo protectant and also to keep the crystals moist for the duration of the looping.

In our FC-43 oil with 12 wt % fluorooctanol system, emulsion droplets were not stable against coalescence. Opening the chip and deposition of new buffer disrupted the emulsion stored in the chip. We found some crystals to remain in the stored wells, or attached to the polytetrafluoroethylene foil 24, while other crystals were freely floating in the puddle of cryo-protectant covering the chip.

We looped crystals using standard Nylon loops (Hampton Research). Looped crystals where immediately cryo frozen by plunging into liquid nitrogen. Crystals remained stored in liquid nitrogen until X-ray diffraction data was collected at the MacChess F1 beam line at Cornell University in a cryostream ($N_2$ (g)). We took 40 consecutive frames with 1° rotation and 1 second exposure for a total of 46 crystals. Most crystals diffracted to better then 1.5 Å resolution. We defined the resolution cut-off to where the Bragg peak intensity dropped below twice the background intensity. The mosaicities for the crystals in our data set fell into a range of 0.2 and 0.4. The best crystal in the set had a diffraction better than the edge of the detector at 1.17 Å with mosaicity of 0.15 to 0.22.

Even though our approach to open the dialysis Phase Chip resulted in mechanical disruption of the emulsion droplets and hence the crystals in them, we could consistently loop high-quality crystals for X-ray crystallography from the chip. To minimize mechanical disruption when opening the chip, the polytetrafluoroethylene sheet 24 for wetting control could be covalently attached to the storage lid 21. This would ensure that droplets would stay intact when retrieving the storage lid from the chip. Each droplet could then be accessed independently.

Conclusions

In this example, we designed a new microfluidic dialysis chip, to kinetically probe phase diagrams in a high throughput manner. Exploiting osmosis and reverse osmosis, we performed proof of principle experiments crystallizing glucose isomerase. We confirm that protein crystallization can be monitored using Second Harmonic Generation and that crystals can be harvested from the chip to collect high resolution X-ray diffraction data. We envision extending the capabilities of the reservoir layer to formulate spatial concentration gradients along one or two dimensions, or to include formulator capabilities. Ultimately we envision applying the dialysis Phase Chip of this example to optimize membrane protein crystallization trials with respect to optimal detergent concentration, which cannot be accomplished in classic crystallization trials. We also envision a dialysis chip compatible with polarization microscopy to be able to investigate assembly and disassembly of biological hydrogels such as intermediate filament assemblies or amyloid fibrils.

Thus, we improved the permeation Phase Chip described in Shim et al., "Using Microfluidics to Decouple Nucleation and Growth of Protein Crystals", *Crystal Growth & Design* 2007, Vol. 7, No. 11, pages 2192-2194, such that the composition of the dialysis membrane can be chosen arbitrarily. The example design of FIG. 1 may include four separate layers in order from top to bottom: (1) a storage layer 21; (2) a wetting control layer 24 (e.g., FEP); (3) a membrane 23; and (4) a chemical potential reservoir 22. A protein solution 27 can be injected in the storage layer 21. The wetting control layer 24 (e.g., FEP) ensures that all walls of the storage loading channels are wetted by the fluorinated oil 39. The wetting control layer 24 (e.g., FEP) may comprise a fluorinated sheet with one perforation at the location of each storage chamber in the first layer. Below the wetting control layer (e.g., FEP) is a dialysis membrane 23. This example dialysis membrane of the invention enables the programmed exchange of pH, salts, surfactants. and other small molecule solutes into and out of the storage layer. This feature greatly extends the range of potential applications for the dialysis chip as it now becomes feasible to conduct cell culture experiments on chip, but also phase diagrams at constant ionic strength can be recorded. We simplified chip manufacturing by adopting a modular design. The device is assembled by clamping together the four pieces. Previously, devices were irreversibly bonded together into a single piece. However, it is also contemplated that the reservoir 22, the membrane 23, the wetting control layer 24 and the storage layer 21 may be laminated together.

The dialysis membrane of the invention has applications in the screening and optimization of kinetic trajectories (e.g., protein crystallization conditions, stem cell differentiation pathways, etc.) and in the mapping of phase diagrams (e.g., colloidal systems, cell viability assays, chemical reaction kinetics, etc.). The dialysis membrane of the invention has advantages including: (1) it is a 100% reusable chip; (2) it is modular such that any kind storage, reservoir and membrane can be combined; (3) samples can be retrieved by easily disassembling the device enabling easy access to the processed samples (e.g., crystals looped. cells harvested); and (4) easy fabrication (embossing with no lidding needed).

Example 2

In this example, we demonstrate microfluidic devices to map protein phase diagrams and nucleation kinetics for in situ x-ray diffraction of protein crystals.

Overview

We developed a technology based on emulsion microfluidics in which 1 nanoliter drops of protein solution are encapsulated in oil and stabilized by surfactant. Crystallization is a stochastic process; we determine nucleation kinetics by measuring thousands of identical drops. We optimize nucleation and growth by generating hundreds of different kinetic paths simultaneously by varying both temperature and concentration of the protein solution. Once the optimal kinetic path is determined, we process an entire emulsion under optimal conditions to generate one crystal per drop. We improved the Phase Chip microfluidic device described at Shim et al., "Using Microfluidics to Decouple Nucleation and Growth of Protein Crystals", *Crystal Growth & Design* 2007, Vol. 7, No. 11, pages 2192-2194. For example, the microfluidic device of this example can operate with a dialysis membrane, allowing us to optimize kinetic trajectories against various small molecule solutes, such as salts, pH and surfactants. Also, the microfluidic device of this example is compatible for in situ structure studies by synchrotron diffraction.

Introduction

There is no guarantee that a given protein has a crystalline phase, but even existence of an equilibrium phase is not sufficient for a crystal to form because the transformation of a protein solution to a crystal is governed by two nonequilibrium processes: nucleation and growth. Consequently, supersaturation kinetics play an essential role in crystallization and we believe that the optimal crystallization strategy should screen kinetic trajectories involving variables such as depth of supersaturation, duration of supersaturation, and sample volume. While other microfluidic crystallization platforms capable of in situ diffraction have been developed, to our knowledge no technique available allows for a systematic and reversible kinetic control of the crystallization trajectory. This entails finding conditions on-chip for which one crystal is grown per drop and then isolating hundreds of drops stored on a x-ray transparent microfluidic chip. Single, non-cryoprotected crystals are too small to collect a complete diffraction set, but a full data set can be obtained by combining many single diffraction patterns.

Figure 4:
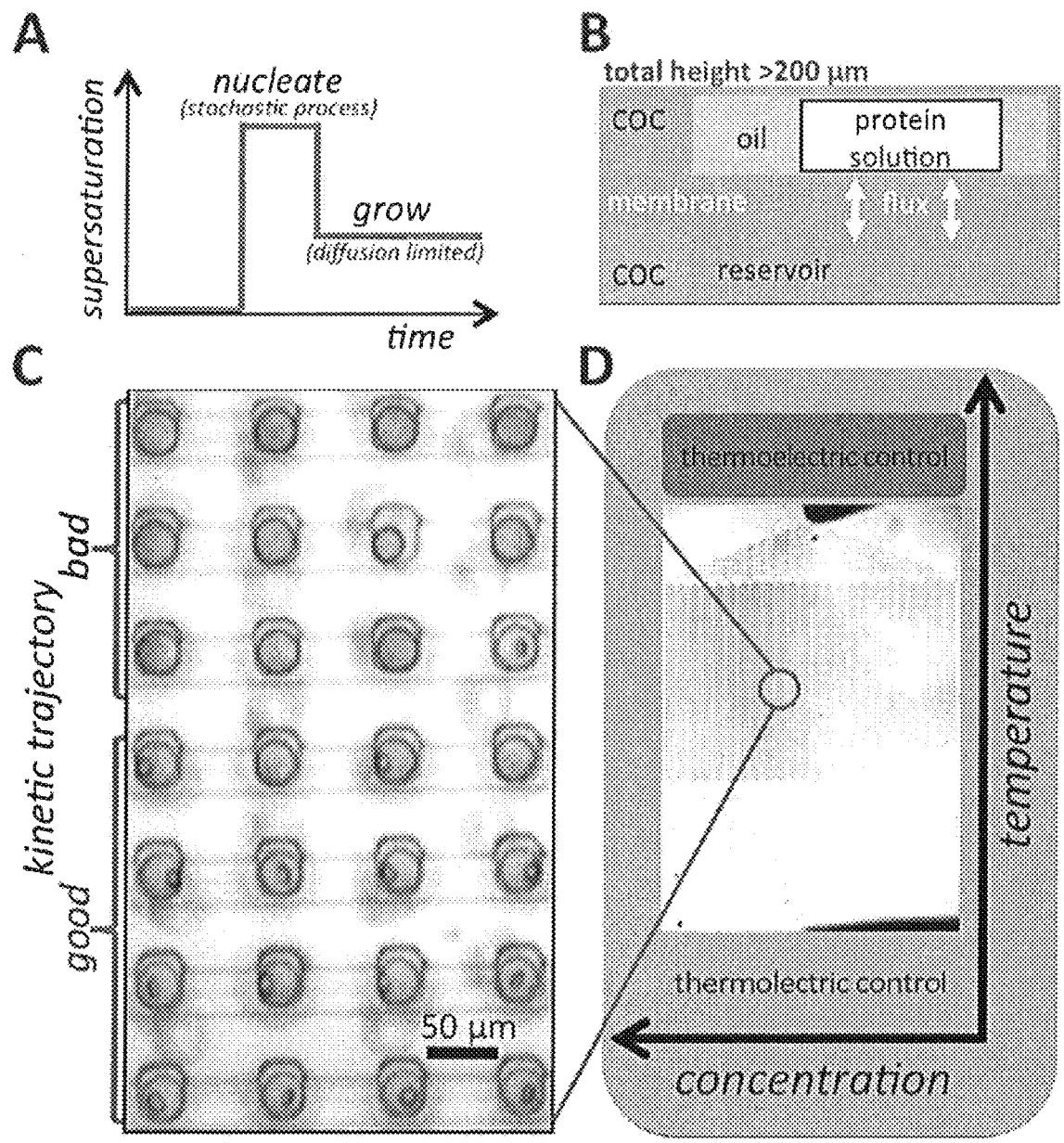
FIG. 4 shows microfluidic technology according to the invention that allow for a systematic and reversible kinetic control of crystallization trajectory.

FIG. 4 shows in (A), ideal crystallization trajectory increases supersaturation until just one crystal nucleates, then decreases supersaturation to prevent further nucleation, but promote crystal growth. In FIG. 4 (B), the stored protein droplet is osmotically coupled to a chemical potential reservoir using a semi-permeable membrane. We use either a dialysis membrane to exchange small molecule solutes and salt, or an elastomeric membrane, to only permeate water and non-polar solutes between both microfluidic layers. With a dedicated sample stage we can simultaneously quench concentration and generate temperature gradients to rapidly screen hundreds to thousands of different kinetic crystallization trajectories in parallel. In FIG. 4 (C), using Lysozyme as a model protein, we find sharp transitions from non-crystallizing to crystallizing trajectories. In FIG. 4 (D), there is shown a schematic top-view of our set-up, illustrating the perpendicular arrangement of temperature and concentration control. Both can be controlled reversibly, allowing us to decouple protein crystal nucleation and growth.

Experimental

The dialysis microfluidic device of this example is built combining standard soft-lithography and replica molding with custom laser cut parts. For fabricating the storage layer, we manufacture an 'inverse' negative resist master where the features are wells surrounded by higher SU8 resist. We mount the wafer into an acrylic casting frame to cast a PDMS replica that can act as a mold for the polyurethane resin (Crystal Clear 204, Smooth-On, Inc.), which once cured forms the storage layer lid. The PDMS reservoir is cast on a traditional SU8 master, where features built up as posts define the channels in the PDMS piece. The chip is then assembled by placing the dialysis membrane between the storage and reservoir layers and clamped together with the help of a matching acrylic back that was cut to shape with a laser cutter.

The X-ray Phase Chip microfluidic device of this example is fabricated by bonding 50 μm thin cyclic-olefin-copolymer (COC) foil (TOPAS®) onto thin PDMS slabs that were fabricated by spin-coating PDMS onto a master. We then peel the storage and the reservoir layer with the COC lids from the master, punch through holes and bond them to a prefabricated ~40 μm thin PDMS membrane such that the PDMS membrane lids both halves of the chip. The X-ray Phase Chip is then mounted into a dedicated acrylic frame with fluid connectors to interface the chip.

Results and Discussion

Figure 5:
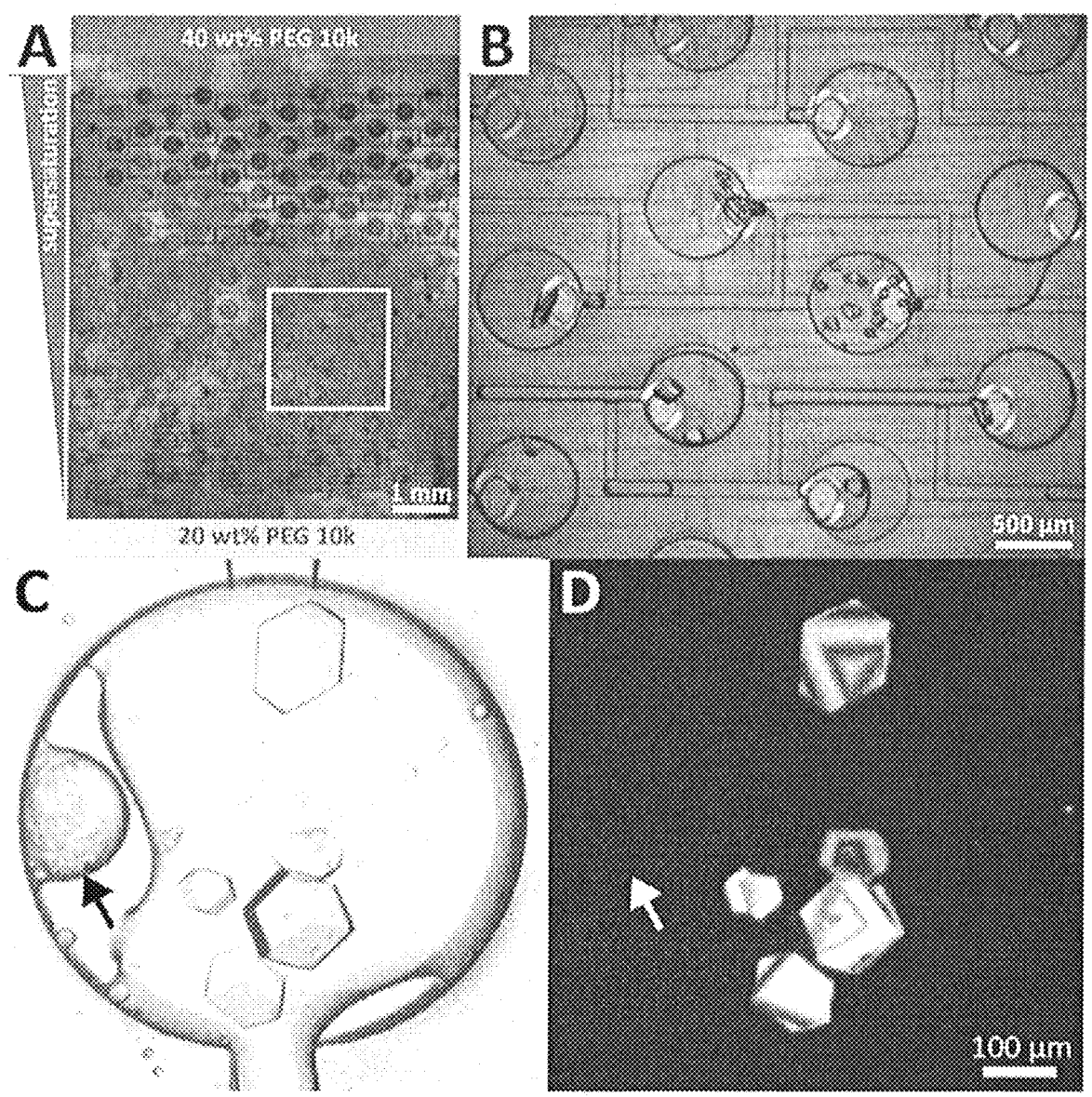
FIG. 5 shows: in (A), 30 mg/ml Glucose Isomerase crystallized against a PEG gradient of 20 to 40 wt % PEG of MW 10,000 in 100 mM Ammonium Sulfate, pH 7.3, notice the shallow depth of the crystallization slot, from no crystals (bottom rows), to single crystals, to multiple crystals per drop to precipitate (top rows); in (B), a close up of inset in (A); in (C), bright field microscopy; and in (D), with Second Harmonic Generation (SHG) images of Glucose Isomerase crystals in the chip. The arrow indicates non crystalline protein aggregates that have no SHG signal.
Figure 6:
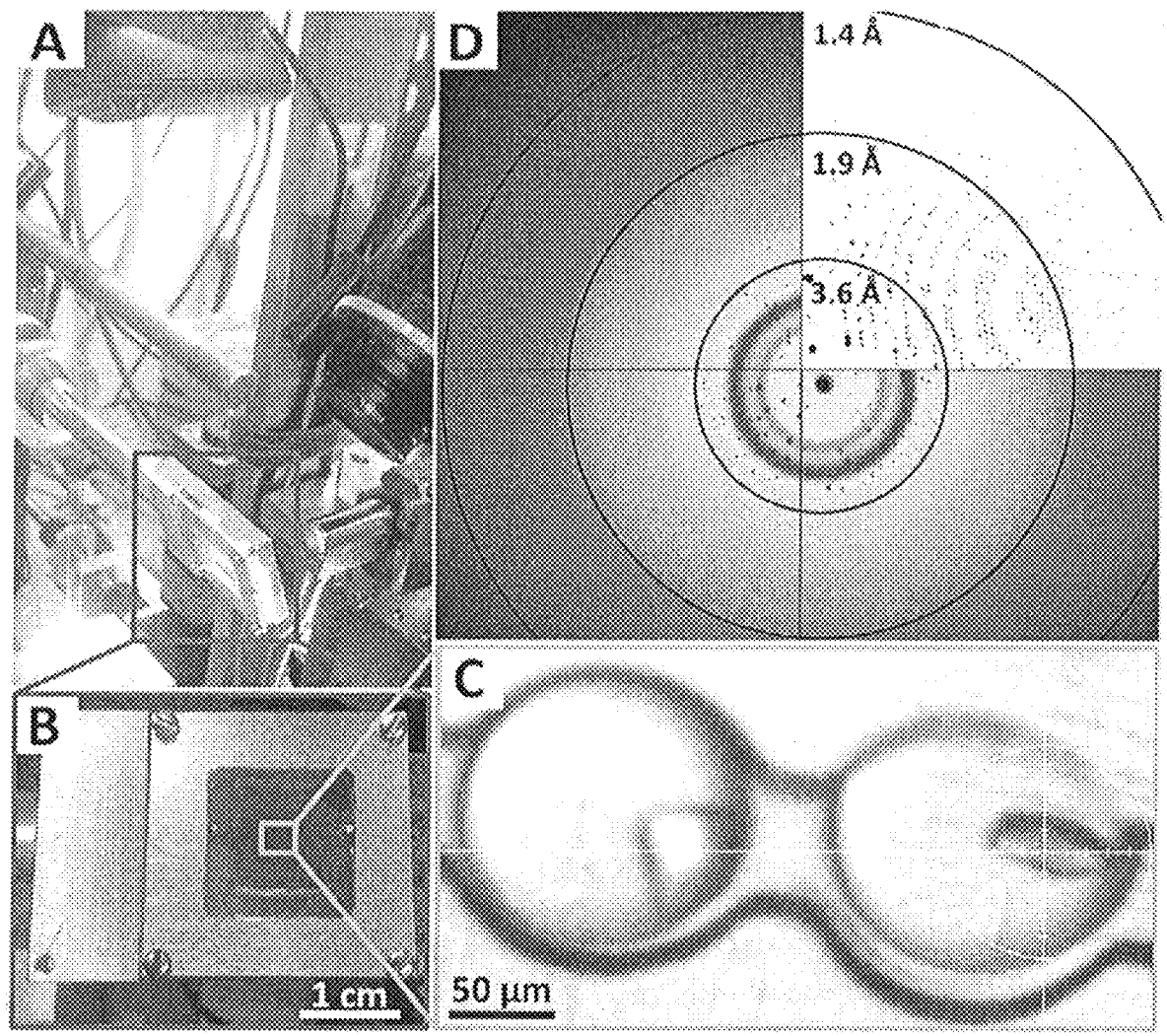
FIG. 6 shows: in (A), an X-ray transparent chip according to the invention inside the Cornell University MacChess F1 beamline; in (B), a custom mount is used to hold the thin foil chip in the beam; in (C), Glucose Isomerase crystals inside of the microfluidic device according to the invention wherein using a motorized stage, each crystal can be centered in the collimated x-ray beam, and the beam is 100 μm in diameter as indicated by the cross-hair; and in (D), a representative diffraction pattern of a Glucose Isomerase crystal taken at room temperature from inside an X-ray chip according to the invention. Crystals diffracted down to 1.37 A resolution with a mosaicity as low as 0.04. The top right quadrant shows the diffraction patterns after background subtraction. A high resolution structure was obtained by merging data from 72 crystals.

As a proof of principle experiment, we crystallized Glucose Isomerase (Hampton Research) in a PEG gradient (see FIG. 5). We optimize kinetic crystallization trajectories using Second Harmonic Generation (SHG) imaging to distinguish amorphous protein aggregates from small crystal clusters (FIGS. 5 C&D). To directly collect diffraction data from crystals grown in chip, we use PDMS-COC hybrid devices that were optimized for low X-ray background (FIG. 6). By encapsulating the crystallization cocktail into emulsion droplets (FIG. 6 C), we yield highly monodisperse crystals, with one crystal per drop. We merged 230 x-ray diffraction image frames taken at room temperature, with one degree rotation each from a total of 70 Glucose Isomerase crystals into a single dataset and solved the structure by molecular replacement down to 1.9 Å resolution (R=0.1579). We took about 5 diffraction frames per crystal with exposure times of 1 second each. Because the crystals were not cryo-frozen, considerable radiation damage was accrued and all diffraction peaks had vanished after 10 to 15 seconds accumulated exposure. Ideally, a dataset merged from more crystals with only single sub-second exposures each would yield a better resolution structure.

Conclusion

As demonstrated in this example, we developed new microfluidic tools to support the protein crystallography community. By incorporating a dialysis membrane into a Phase Chip microfluidic device, we can screen hundreds to thousands of different crystallization conditions with complex kinetic trajectories in parallel. Thus, we can optimize crystallization recipes to grow monodisperse crystals, with one crystal per drop. These crystal emulsions can then be transferred to the X-ray transparent chip, to collect room temperature diffraction data from many identical crystals. The dialysis Phase Chip microfluidic device of this example enables new avenues for single cell and small population chemostat experiments, or multiplex perturbation reactors to map nonlinear chemical kinetics of complex reaction networks as found in many biochemical pathways.

Example 3

In this example, we demonstrate room temperature serial crystallography using a kinetically optimized microfluidic device for protein crystallization and on-chip X-ray diffraction.

Overview

In this example, we demonstrate that we have developed an emulsion based serial crystallographic technology in which nanoliter sized droplets of protein solution are encapsulated in oil and stabilized by surfactant. Once the first crystal in a drop is nucleated, the small volume generates a negative feedback mechanism that lowers the supersaturation, which we exploit to produce one crystal per drop. We diffract, one crystal at a time, from a series of room temperature crystals stored on an X-ray semi-transparent microfluidic chip and obtain a complete data set by merging single diffraction frames taken from different unoriented crystals. As proof-of-concept, we solved the structure of glucose isomerase to 2.1 Å, demonstrating the feasibility of high-throughput serial X-ray crystallography using synchrotron radiation.

1. Introduction

In conventional protein X-ray crystallography, a complete data set is ideally obtained from a single crystal, which typically requires a relatively large crystal that has been successfully cryocooled. Serial crystallography takes the opposite approach: complete diffraction sets are assembled from a large number of individual diffraction frames acquired from small, single, unoriented crystals that are not cryoprotected. Complete coverage of the Ewald sphere is obtained by assembling individual diffraction frames into a single data set. The ideal crystals for serial crystallography are large enough and sufficiently defect free to diffract to high resolution, are produced in large quantity, and are sufficiently identical to facilitate merging of diffraction frames.

Serial crystallography with non-cryocooled crystals has several technical advantages over conventional methods. First, the crystals can be small, which increases the potential for growing crystals in the first place. Second, it avoids the roughly ten-fold increase in crystal mosaicity typically encountered during cryoprotection and eliminates the need to search for cryoprotectant conditions. Although non-cryoprotected crystals suffer radiation damage at a roughly hundred times higher rate than cryoprotected crystals, there is little disadvantage associated with using many non-cryocooled crystals to obtain a complete data set if the crystals are easy to produce, plentiful, and easy to handle.

Figure 7:
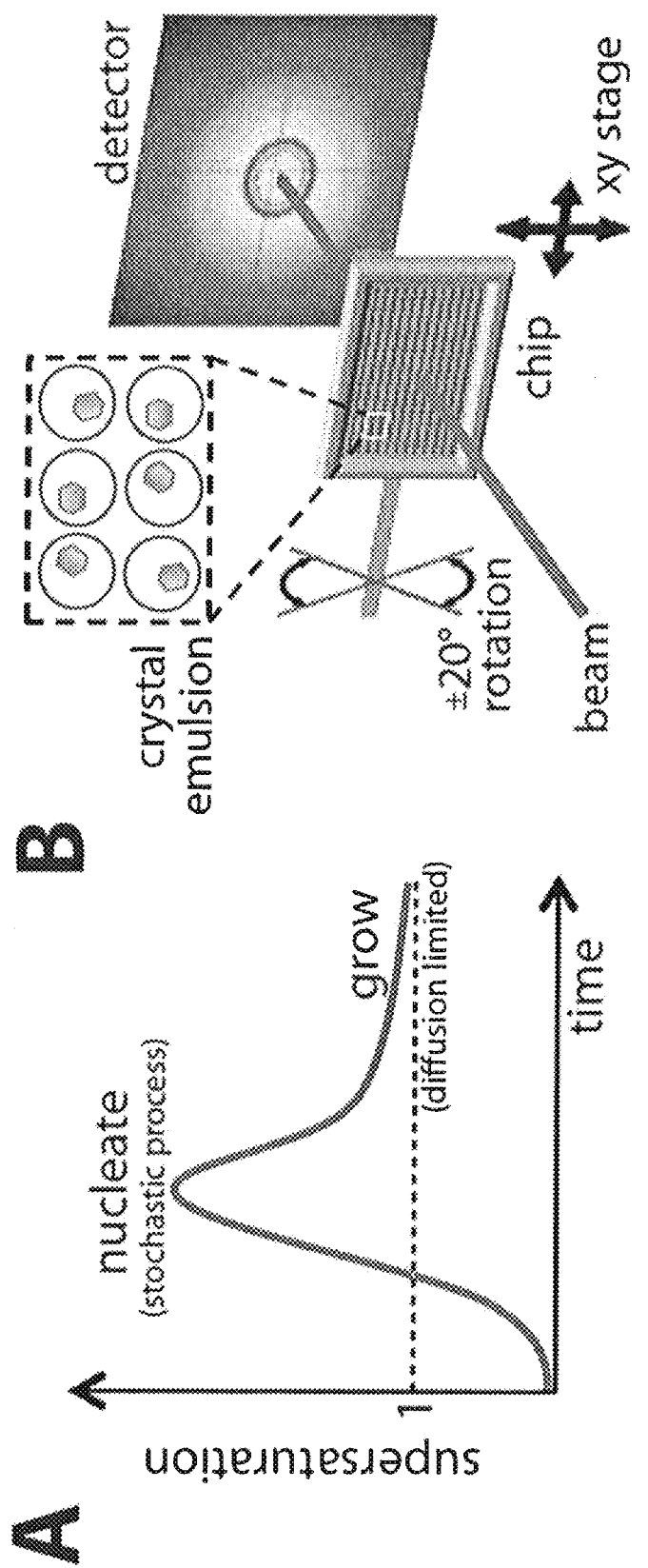
FIG. 7 shows: in (A), optimal crystallization trajectory increases supersaturation until just one crystal nucleates, then decreases supersaturation to prevent further nucleation, while remaining supersaturated enough to promote crystal growth; and in (B), emulsion droplets with monodisperse crystals were stored in an X-ray semi-transparent microfluidic device according to the invention wherein sequentially collected diffraction frames from multiple individual crystals were merged to solve the protein structure. The chip could be translated in x- and y-directions and rotated ±20°.

The ideal crystallization procedure, illustrated in FIG. 7(A), to produce protein crystals for any form of crystallography, including serial crystallography, comprises slowly increasing the supersaturation of a protein solution until the moment that a single crystal is nucleated. Then, once the first nucleation event occurs, the supersaturation is reduced enough to prevent further nucleation, while remaining supersaturated enough to grow the crystal. Ideally, the growth conditions should be slow enough to allow for annealing of defects, and the procedure must be capable of producing crystals in large numbers and of identical size. Additionally, the technology to produce crystals must be simple and inexpensive if serial crystallography is to become adopted by the structural biology community.

The challenge is to design such a method. The well known Counter-Diffusion method produces a series of kinetic supersaturation profiles that rise and fall as illustrated in FIG. 7(A). However, both the time at which the supersaturation maximum occurs and the value of the supersaturation maximum are independent of the nucleation event. The maximum supersaturation varies along the capillary length and with a long capillary the chances are improved that somewhere along the capillary there will be a location where the maximum supersaturation will coincide with the first nucleation event. However, this method requires long capillaries and is not optimal for volumes under 1 nanoliter. Furthermore, Counter-Diffusion requires that the precipitant and protein have greatly different diffusion constants, so it is suitable for low molecular weight precipitants, such as salt, but not for macromolecules, such as poly(ethylene glycol) (PEG).

Another issue complicating design of the ideal profile of FIG. 7(A), is that at constant supersaturation nucleation is a random process, rendering it impossible to a priori know when to decrease supersaturation, which should coincide with the first nucleation event. One way to generate the ideal supersaturation profile would be to monitor the supersaturated solution with a technique, such as Second Harmonic Generation (SHG) microscopy, that is sensitive to the formation of small crystals and then, once the first crystal is detected, lower the supersaturation. However, this scheme will be cumbersome to implement in the high throughput case of processing hundreds to thousands of samples. An alternative method is desired.

Microfluidically produced, monodisperse, emulsions have previously been used to produce drops of supersaturated protein solution in which each drop nucleates a single crystal. This situation is ideal for serial crystallography for a number of reasons. Since only one crystal nucleates per drop, all the supersaturated protein in solution is delivered to a single crystal, making that crystal as large as possible. Microfluidic precision allows preparation of emulsion droplets with variations in size of a few percent only, even at high flow rates. Furthermore, because of the small length scales in microfluidics, convection is suppressed and flows are laminar. Taken together, processing proteins using microfluidics leads to crystals of the uniform size that are grown under identical conditions, which has the effect of creating crystals that have similar characteristics, such as unit cell and degree of disorder. Having identical crystals facilitates merging of diffraction data sets taken from different crystals.

In the microfluidic device described in this example, we first produce drops containing protein. Then, exploiting surface tension forces, we guide drops to 8,000 storage sites on-chip. Next, we increase supersaturation to induce crystallization in such a way as to produce one crystal per drop. Finally, we sequentially collect diffraction from individual crystals and merge data sets in order to solve the protein structure (see FIG. 7B).

Producing and diffracting from crystals in the same device eliminates the laborious and potentially damaging steps of looping and extracting the crystal from the mother liquor. Various microfluidic crystallization platforms compatible with in situ diffraction have been developed. However, these devices incorporated valves in the chip, thus rendering them expensive to manufacture and difficult to operate. Other technologies are low-throughput, or need a second round of scale-up to larger capillaries to produce crystals large enough to collect diffraction data.

2. One Crystal Per Drop Through Compartmentalization

The production of one crystal per drop is a result of a competition between two processes, nucleation and growth, in a confined volume. Both processes require supersaturation and therefore both nucleation and growth are nonequilibrium processes. When the first nucleus forms inside the drop, it decreases the supersaturation in the surrounding protein solution as the crystal grows. If the rate of nucleation is low enough, then the growing crystal will consume enough of the protein in solution to decrease the supersaturation to the point where another nucleation event is improbable. Further nucleation is prevented if the time for a protein to diffuse across a drop is less than the time to nucleate a crystal. Thus combining a small drop volume with the physics of nucleation and growth, generates negative feedback that acts to autonomously create the ideal dynamical supersaturation profile that produces one crystal per drop. Instead of having the negative feedback imposed externally, as in the Second Harmonic Generation microscopy scheme discussed previously, here the negative feedback is engineered into each drop; no external intervention is required. All the engineering goes into identifying the correct combination of diffusive flux, nucleation rate and drop volume for the emulsions. To complete this screen efficiently, we use polydisperse emulsion droplets as detailed in the next section.

In this section we calculate the drop volume such that only one crystal is nucleated per drop. Consider a drop that contains a supersaturated solution that has not nucleated any crystals. As long as the physical-chemical environment is constant, the nucleation rate, J [# of crystals per unit volume, V, and per unit time, t], will also be constant and the probability, P, of nucleating a crystal in a drop of volume V in an infinitesimal time interval $\tau$ is independent of the time, t, $$P(t,t+\tau)=JV\tau, \quad (1)$$

from which it follows that the probability that a drop has not nucleated any crystals is $p(t)=e^{-JVt}$. If, by some contrivance, each drop could only produce one crystal, then since the probability of not crystallizing and the probability of crystallizing have to add to one, we have an expression for the average number of crystals per drop as a function of time;

$$x(t)=1-e^{-JVt}. \quad (2)$$

However, once a drop does nucleate a crystal, the nucleation rate is reduced due to the growing crystal consuming protein in solution and nucleation ceases to be a Poisson process, which makes finding an analytical solution to the number of crystals per drop as a function of time a difficult problem.

To address the question of how many crystals nucleate per drop as a function of drop size, we developed a Monte Carlo simulation in one dimension, a special case for which the drop size and volume are equal. Our approach differs from that taken previously in that our model explicitly calculates the spatial-temporal concentration profile within the drop. Drops were modeled as a lattice of points, where each point was characterized by two quantities; the protein number concentration, c(x, t) [L$^{-3}$], and a binary indicator that signified whether the protein was in a crystalline or solution state. The protein was confined in the drop, meaning that no-flux boundary conditions were imposed on the ends of the lattice. The numerical values used in the model, while within an order of magnitude of values used in our experiments, were not reflective of any particular protein or physical set of conditions. Rather they were chosen for two purposes. First, to satisfy the assumptions of the theory, i.e. that the rate of crystal growth was much larger than the rate of nucleation. Second, to ensure that the simulations were quick to perform. Thus the diffusion constants and nucleation rates were chosen to be higher than actual values. This means that the simulations were faster to perform, but that they conclusions were not affected as they depend on the ratio of the diffusion rate to nucleation rate and not on their absolute values. Protein concentrations in solution evolved according to the diffusion equation; $\delta c/\delta t = -D\nabla^2 c(t)$, with $D=6\times10^{-10}$ [m$^2$s$^{-1}$], the protein diffusion constant. Initially the drop was homogeneous in protein number concentration, c=1 μm$^{-3}$, at a high value of supersaturation, s=83.3, with s=c/c$_s$, with c$_s$=0.012, the concentration of the saturated protein solution in equilibrium with the protein crystal, and with l=1 μm, the size of a lattice site. At each time step, there was a finite probability that a randomly chosen lattice site could transform into a crystal with a probability, P, given by P=Jl$^3$τ and τ=l$^2$/D the simulation time step. In the simulation we used the classical nucleation theory expression for nucleation rate, J=sAe$^{-B/ln(s)^2}$, where A and B are constants such that P=sR666e$^{-350/ln(s)^2}$, with R a dimensionless rate coefficient. The protein concentration of a lattice site coinciding with the edge of a crystal was increased at a rate proportional to the supersaturation according to $\delta c/\delta t = v(c(t)-c_s)/l$, where v=1×10$^{-3}$ [ms$^{-1}$] is the constant velocity of crystal growth. Conservation of mass was used at the boundary between the crystal and solution. The concentration per lattice site in a growing crystal was limited to an arbitrary value of c$_{xtal}$=4 to model the effect that protein crystals have a fixed density that is of order 100 c$_s$. Once a lattice site exceeded this maximum concentration, the crystal would grow symmetrically, one lattice site to the right and to the left. It was assumed that crystals were stationary once nucleated.

FIGS. 8(A) and 8(B) show the simulation results. Parameters were chosen to approximate our experiments; high supersaturation, fast growth, and drops of order 100 μm diameter. In each case, the simulation begins by instantly quenching the drop to a supersaturation of 83. The two figures are taken after nucleation has occurred, but before equilibrium is achieved. In FIG. 8(A), the nucleation rate is low, R=1 in dimensionless units. In what follows, time, t, is non-dimensionalized by τ=l$^2$/D, and distance is nondimensionalized by l=1 μm. The red dashed line indicates the initial condition, at c=1, while FIG. 8(A) occurs at t=250. The crystal that nucleated first is centered at l=19. The width of the crystal increases as protein from solution is fed into the crystal. Later a second crystal is independently nucleated. The growing crystals deplete the protein concentration in the region bordering the crystals. In equilibrium the protein concentration remaining in solution will be homogeneous and equal to the saturation concentration. FIG. 8(B) differs from the conditions of FIG. 8(A) in that the dimensionless nucleation rate is higher, R=27. More crystals are formed, even though the duration of the quench at which FIG. 8(B) is recorded, t=50, is less than in FIG. 8(A). The protein in solution has obtained the equilibrium value in between the two rightmost crystals. A noteworthy observation is the development of a depletion zone in the neighborhood of each growing crystal. If the local concentration is reduced sufficiently, then no additional crystals will nucleate in the depletion zone. The size of the depletion zone is different between the two figures; therefore the depletion zone is a function of the nucleation rate J.

FIG. 8(C) shows the average number of crystals per drop as a function of time obtained from the simulation and compared with a fit to $$\langle x(t) \rangle = x_\infty (1 - e^{-kt}). \tag{3}$$

The simulation conditions were identical to the conditions of FIGS. 8(A) and 8(B); a drop size of 60 μm, and two nucleation rates, R=27 and R=1. The simulation and fit to Equation 3 overlap completely. Equation 2 has two fitting parameters, x$_\infty$, the final number of crystals per drop and k, the non-dimensional rate at which crystals form. FIG. 8(D) shows how the final number of crystals per drop varies a function of drop size for two nucleation rates, R=27 and R=1, while FIG. 8(E) shows how the dimensionless rate, k, varies with size.

FIGS. 8(A) and 8(B) of the concentration profile inside a supersaturated drop of protein solution during crystallization are suggestive of a depletion zone in the vicinity of a growing crystal in which the supersaturation is reduced sufficiently such that no new crystals can be nucleated. Let w be the width of this depletion zone and let τ be the time interval for which the average number of crystals nucleated in a volume w$^d$, is one, where d is the spatial dimension. Then, from Equation 1 it follows $$Jw^d\tau = 1, \tag{4}$$

which provides one equation relating the depletion zone to the nucleation time. In order for no additional crystals to nucleate in the depletion zone, the protein in solution must be able to diffuse through the depletion zone to the growing crystal, thereby lowering the supersaturation in the depletion zone, in less than the depletion time. This provides a second equation between the depletion one and nucleation time, $$\tau = \frac{w^2}{D}. \tag{5}$$

To be self-consistent, we combine Equations 4 and 5, which yields $$w^{d+2} = \frac{D}{J}. \tag{6}$$

FIG. 8(D) shows the simulated dependence of the number of crystals per drop, x$_\infty$, as a function of drop size in one dimension, d=1, for which w=(D/J)$^{1/3}$. Examine the curve with the higher nucleation rate, R=27. For small drops, less than drop size ~9, the number of crystals per drop remains constant at x$_\infty$=1. "Small" means V<w$^d$, i.e. the time for protein to diffuse the entire length of the drop is less than the nucleation time, so that after one crystal has been nucleated, its growth causes a negative feedback suppressing further nucleation throughout the entire drop. As the size of the drop is increased beyond the depletion zone, w, $x_\infty$ becomes greater than one and the number of crystals per drop grows linearly with drop size. Each nucleation event produces a new depletion zone with just one crystal inside. This process repeats until the entire drop is filled with crystals, each occupying a part of the drop equal to the depletion zone, w. This scenario predicts that the number of crystals per drop is $$x_\infty = \frac{V}{w^d} = V\left(\frac{J}{D}\right)^{\frac{d}{d+2}}. \quad (7)$$

The dashed lines in FIG. 8(D) show this behavior; the lines start at the origin and have slope 1/w. The ratio of nucleation rates in the two examples shown in FIG. 8(D) is 27, and as $1/w \propto J^{1/3}$, the prediction is that the ratio of the slopes of the dashed lines in FIG. 8(D) is 3, as observed. Furthermore, the width of the depletion zone scales as $w \propto J^{-1/3}$. Thus for the drop in FIG. 8(D) with slow nucleation rate R=1, the width of the depletion zone, manifested by the drop size for which $x_\infty$ first becomes greater than one, is predicted to be three times greater h tan the depletion zone of the drop with the fast nucleation rate R=27, as observed in FIG. 8(D).

As the drop volume, V, is increased from zero, the rate, k, of nucleating one crystal in V will increase linearly with drop volume as predicted by Equation 1 for Poisson processes $$k_v = \frac{1}{\tau} = JV \quad (8)$$

the behavior seen in FIG. 8(E). However, once the drop volume exceeds the volume of the depletion zone, a crystal will be nucleated somewhere else in the drop; therefore the frequency at which depletion zones are created is $$k = \frac{1}{\tau} = Jw^d = J^{\frac{2}{d+2}}D^{\frac{d}{d+2}}. \quad (9)$$

Equations 6 and 9 predict that $k \propto J^{2/3}$ in one dimension and that k becomes independent of drop size V, as seen in FIG. 8(E).

Figure 8:
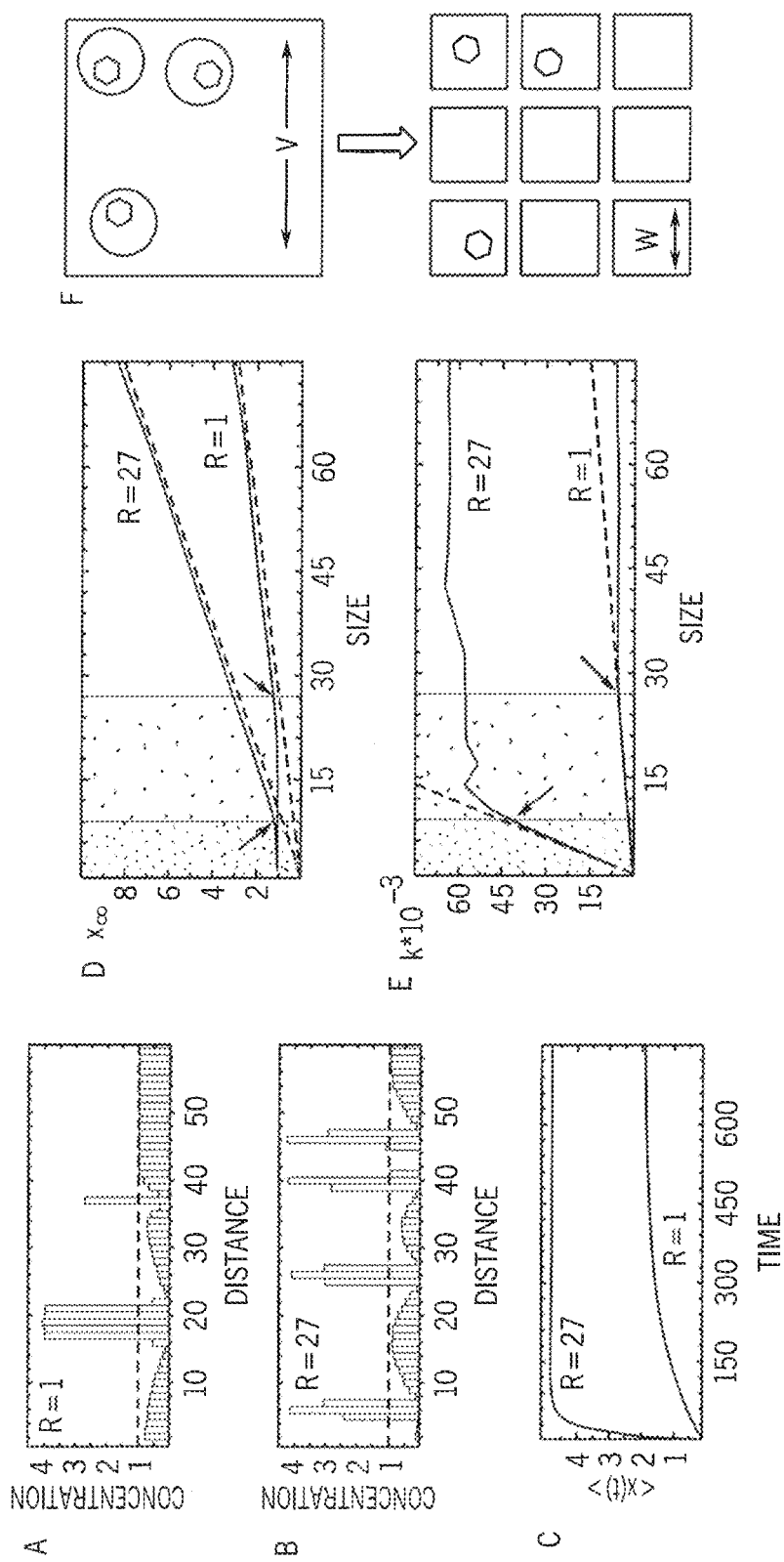
FIG. 8 shows in A and B, protein concentration as a function of distance from a simulation of nucleation and growth in one dimension. Concentration is dimensionless. The dotted line indicates the initial concentration with a supersaturation of 83.3 at t=0. The sites with concentrations that exceed the line are in the crystalline phase, while those below are in solution. In (A), concentration profile at t=250. Slow nucleation rate of R=1 in dimensionless units. In (B), concentration profile at t=50. Fast nucleation rate of R=27. In (C), average number of crystals per drop as a function of time, (x(t)), for two nucleation rates obtained from simulation and fitted to Equation 3, $(x(t))=x-(1-e^{-kt})$. Conditions are the same as in (A) and (B). In D and E, fitting parameters to Equation 3 as a function of drop size for two nucleation rates, R=27 and R=1. Arrows indicate size of depletion zone. In (D), the solid lines are the simulated final number of crystals per drop, x–. Dashed lines are Equation 7, $x-=V=w^d$. In (E), the solid lines are the simulated rate of crystal formation, k. Dashed lines are Equation 8, k=JV. In (F), a conceptual schematic is shown. A drop of volume V can be thought of as x– smaller, independent drops of volume $w^d=V/x\infty$.

The picture that emerges from these simulations and dimensional analysis suggest that nucleation of multiple crystals in a drop is a Poisson process. This is an unexpected result as the nucleation rate is not constant: once the first crystal has nucleated, its growth acts to suppress further nucleation. However, we argue that each nucleation event creates a depletion zone in which it is only possible for one crystal to exist. Therefore, each nucleation event is an independent process. In effect, each drop can be thought of as being partitioned into $x_\infty$ smaller, independent drops of volume $w^d = V/x_\infty$ that nucleate with rate k (FIG. 8 F). This justifies Equation 3, and explains why in FIG. 8(C), the number of crystals per drop as a function of time is an exponential, a result of a Poisson process.

The degree to which growing crystals create depletion zones is expected to be greatest in one dimension. For example, in one dimension no protein can be replenished in the gap between two crystals, while in higher dimensions, protein will diffuse into the gap between two crystals along the directions perpendicular to the line connecting the center of the crystals. Nevertheless, we expect the same general trends observed in 1D to carry over to 2D and 3D. In particular, in dimension d we expect there will be a drop volume $$V_d \sim (D/J)^{\frac{d}{d+2}},$$

below which only one crystal will be nucleated per drop.

3. Crystal Emulsions

To yield identical crystals in sufficient quality and quantity for serial crystallography, we use a two step method. We first identify the appropriate drop volume to consistently nucleate one crystal per drop. For this we intentionally created emulsions in a batch process that yielded a polydisperse size distribution, ranging from a few microns to a few hundreds of microns in diameter (FIG. 9A-C). Such a polydisperse emulsion allowed us to identify the critical diameter in a single screening experiment. We then used microfluidics (FIG. 9D) to produce monodisperse emulsion droplets (FIGS. 9E, 9F), which we used to grow identical crystals in the serial X-ray diffraction chip, as described in section 5 below. For the purposes of this example, however, the full experimental sequence will only be reported for glucose isomerase, i.e., whereby crystals were grown in the serial diffraction chip, X-ray data were acquired, and the structure was solved.

Figure 9:
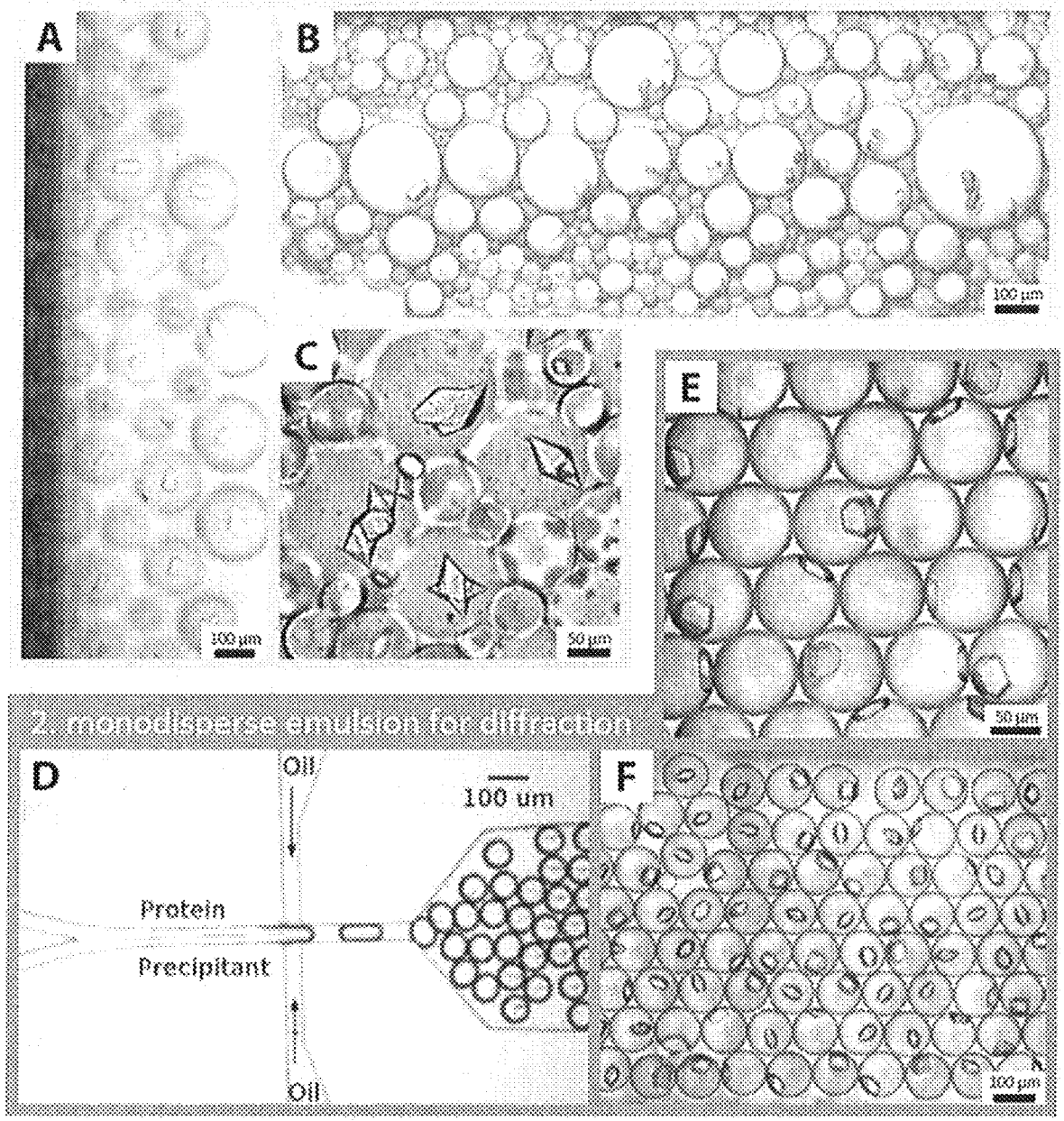
FIG. 9 shows protein crystallization in emulsion droplets stabilized by surfactant. Ideal drop sizes were first identified using polydisperse emulsion droplets. Monodisperse emulsion were used to produce identical crystals for diffraction experiments. Droplets were stored in a rectangular glass capillary. In A to C, polydisperse emulsions of: (A) D1D2 heterodimer from human spliceosomal snRNP particle, (B) concanavalin A, and (C) trypsin. In (D), protein and precipitant solutions were introduced in a co-flow geometry under laminar flow conditions that prevent mixing upstream of the nozzle where both solutions became encapsulated into emulsion droplets. In E and F, monodisperse emulsions of (E) glucose isomerase and (F) lysozyme crystals.

All crystals were grown in emulsion droplets stabilized against coalescence with a 2% v/v solution of PFPE-PEG-PFPE non-ionic triblock surfactant "E2K0660" in Novec™ HFE-7500 fluorinated oil (from 3M). The PFPE-PEG-PFPE surfactant was synthesized as previously described in Holtze et al., (2008) Lab on a Chip, 8(10), 1632-9. PFPE is a perfluorinated polyether, —CF(CF$_3$)CF$_2$O—, and polyethyleneglycol (PEG) is —CH$_2$CH$_2$O—. Note that a commercial surfactant is now available from RAN Biotechnologies, Beverly, Mass., USA. Novec™ HFE-7500 is 2-(Trifluoromethyl)-3-ethoxydodecafluorohexane. We chose a fluorinated oil and a fluorinated surfactant to minimize interactions with biological molecules. Fluorocarbon and hydrocarbon oils do not mix with each other, nor do they mix with water. In particular, the PFPE-PEG-PFPE surfactant in HFE-7500 oil system has been shown to have excellent bio-compatibility. To confirm that it is compatible with protein crystallization, we tested it with five crystallization model proteins (FIG. 9 and Table 1). All five model proteins have previously been crystallized by vapor diffusion and a structure derived from X-ray crystallography deposited in the PDB.

TABLE 1

|  | formula weight | Isoelectric point (pI) | net charge in crystal |
|---|---|---|---|
| Lysozyme | 14.3 kDa | 11.3 (from (Wetter & Deutsch, 1951)) | positive |
| Trypsin | 24 kDa | 10.1-10.5 (From (Walsh, 1970)) | positive |
| Concanavalin A | 76.5 kDa (3mer) | 4.5-5.5 (multiple isoforms, see (Entlicher et al., 1971)) | negative |
| Glucose isomerase | 173 kDa (4mer) | 3.95 (from (Vuolanto et al., 2003)) | negative |

TABLE 1-continued

|  | formula weight | Isoelectric point (pI) | net charge in crystal |
|---|---|---|---|
| D1D2 | 26.8 kDa (heterodimer) | 10.6 (theoretical pI, from (ProtParam tool, 2013)) | positive |

To adopt a published vapor diffusion recipe into our emulsion format, we had to perform a set of pre-experiments. In traditional vapor diffusion, a small volume of protein solution is mixed with the same amount of precipitant and then sealed into a container together with a large reservoir of precipitant. The diluted protein-precipitant drop equilibrates through vapor phase diffusion with the reservoir, resulting in a concentration increase of all components in the drop by approximately a factor of two. All previously published crystallization recipes had been optimized to nucleate only a few crystals per microliter. Our emulsion droplets have volumes of a few picoliters to nanoliter each. As the probability of nucleating a crystal is proportional to the sample volume, we had to increase nucleation rates by at least two orders of magnitude. We thus prepared vapor phase and microbatch crystallization trials around the literature recipes and optimized the vapor recipes toward nucleating crystal showers of appropriate density. When attempting to crystallize a novel protein target through screening crystallization conditions such crystal showers are usually considered a first hit and the conditions are later refined extensively to grow the largest possible crystal. When using the method presented here on a novel protein target, the polydisperse emulsion screen would directly follow onto the initial hit finding, and therefore eliminate the reverse engineering step of converting an optimized vapor phase recipe back to a recipe that grows crystal showers.

Polydisperse emulsions were then prepared by mixing 2 µL protein solution with 24 precipitant in a 150 µL PCR test-tube. Immediately after mixing, we added 30 µL 2% v/v solution of PFPE-PEG-PFPE surfactant (E2K0660) in HFE-7500 fluorinated oil. Polydisperse emulsions were formed by gently agitating the vial by hand until droplets became too small to be resolved by eye. This procedure typically gave droplets ranging from a few microns to a few hundreds of microns in diameter (FIG. 9A-C). Aqueous droplets were less dense then the immersing fluorinated oil, so droplets rose ("creamed") to the top of the vial within a minute. The emulsion cream was then loaded into rectangular glass capillaries (VitroTubes from VitroCom, Mountain Lakes, N.J., USA) and sealed with 5 minute epoxy to prevent evaporation. Crystallization was monitored over the course of a week. All compounds and proteins from commercial sources were used as received without further purification. The molecular weight and the net charge of the proteins during crystallization, as derived by the isoelectric point, are summarized in Table 1.

Lysozyme was crystallized by encapsulating 30 mg/ml Lysozyme, 100 mM sodium acetate, pH 4.8, 12.5 wt % PEG 8000, 5 wt % NaCl final concentration into droplets and then incubating them at 6° C. for 36 hours until all droplets had nucleated crystals. This recipe was derived from a vapor phase recipe mixing 20 mg/ml lysozyme in 100 mM sodium acetate pH 4.8 with an equal volume 10% (w/v) NaCl, 100 mM sodium acetate pH 4.8, and 25% (v/v) ethylene glycol.

Glucose isomerase crystals were grown at room temperature (~25° C.) by preparing a crystallization batch with final concentrations of 30 mg/ml glucose isomerase from *Streptomyces rubiginosus* (from Hampton Research), 100 mM ammonium sulfate, pH 7.0, 20 wt % PEG 10,000 in a 1:1 ratio (all from Sigma Aldrich). The initial vapor phase crystallization condition was taken from the Hampton Research data sheet as mixing 20-30 mg/ml glucose isomerase with 10 to 15% (w/v) PEG 4000-8000, 200 mM salt, pH 6.0-9.0.

Trypsin was crystallized by mixing 60 mg/ml trypsin (Sigma T-8253) from bovine pancreas in 10 mg/ml benzamidine, 3 mM $CaCl_2$, 0.02 wt % sodium azide with 100 mM $NaPO_4$, pH 5.9, 5.1 M ammonium acetate (all Sigma Aldrich). In this system we observed crystals in the range of pH 5.9 to pH 8.6, with higher pH values having much higher nucleation rates. This recipe was derived from a vapor phase recipe mixing 60 mg/ml trypsin in 10 mg/ml benzamidine, 3 mM calcium chloride, and 0.02% (w/v) sodium azide with an equal volume of 4% (w/v) PEG 4000, 200 mM lithium sulphate, 100 mM MES pH 6.5, and 15% ethylene glycol.

Concanavalin A was crystallized by mixing 25 mg/ml concanavalin A type IV from *Canavalia ensiformis* in 10 mM tris hydrochloride, pH 7.4 with 100 mM tris hydrochloride, pH 8.5, 8 wt % PEG 8,000 in a 1:1 ratio (all from Sigma Aldrich). For this we first set-up vapor phase and microbatch trials of 20 mg/ml Concanavalin A in 10 mM TRIS pH 7.4 against the 50 conditions in the Hampton Crystal Screening Kit. From this screen we choose condition 36, with 100 mM tris hydrochloride, pH 8.5, 8 (w/v) PEG 8000, as this condition grew crystals in both vapor phase and microbatch trials.

D1D2, the sub-complex from the human snRNP spliceosome core particle (PDB entry 1B34), crystallized over 72 hours at room temperature by preparing a crystallization batch with final concentrations of 6 mg/ml D1D2, 62 mM sodium citrate pH 5.2, 125 mM ammonium acetate, 9 vol % glycerol, 26 wt/vol PEG 4,000 (all Sigma Aldrich). D1D2 was purified as previously reported. D1D2 was first crystallized by Kambach et al. in vapor phase by mixing equal volumes of 6 mg/ml D1D2 in 20 mM sodium HEPES pH 7.5, 200 mM sodium chloride and 6 mM dithiothreitol and 100 mM sodium citrate pH 5.6, 200 mM ammonium acetate, 15% glycerol, 25% PEG 4000.

All globular proteins, concanavalin, glucose isomerase and trypsin, crystallized readily in vapor diffusion, microbatch, and the emulsion system. The heterodimer D1D2 formed crystals in vapor phase and the emulsion system only. In microbatch, a thick protein skin grew at the droplet interphase potentially depleting all the protein from the drop. We thus conclude that the PFPE-PEG-PFPE surfactant system is well suited to protect protein from absorbing to the fluorooil-water interface and to stabilize emulsions, making it ideal for crystallization trials.

All initial crystallization experiments were performed at room temperature. However, a particular protein may become unstable at too high or too low temperatures. Also, many proteins like lysozyme have temperature sensitive nucleation rates, which one might like to exploit in crystallization trials. An ideal surfactant oil system can hence be used in a large temperature range. To test for temperature compatibility, we prepared crystal emulsions from the PFPE-PEG-PFPE surfactant in HFE-7500 oil, sealed them into rectangular glass capillaries and incubated them in a water bath at 4° C. and at 40° C. We found the emulsion droplets to be stable for at least two weeks at those two temperatures.

Finally, to yield identical crystals in sufficient quantity for serial crystallography, we employed microfluidics to produce monodisperse emulsion droplets. For this, we simply selected the dropmaking chip appropriate to make drops of the desired diameter and used the crystallization recipe from the preceding polydisperse emulsion screen without further modification. We produced drops in a co-flow geometry designed such that the protein solution and buffer do not mix in the laminar flow upstream of the dropmaker (FIG. 9D). Typically, injection of the oil-surfactant mixture proceeded at 600 μL/hr, while both protein and precipitant streams were pumped at equal flow rates of 300μ/hr to co-encapsulate both in a 1:1 mixture. Upon droplet formation, mixing inside each droplet proceeds within less than a second due to recirculating flow that arises from shearing interactions of the fluid inside the drops with the stationary wall. These monodisperse emulsion droplets were then injected into and incubated in the diffraction chip to grow crystals for the X-ray diffraction experiments.

To monitor crystallization, we stored emulsion droplets in two different systems. Firstly, polydisperse emulsions were usually sealed into rectangular glass capillaries, which prevented water and oil evaporation. Secondly, as our diffraction chip was made from a polymer material, we exploited its permeability to water vapor by slowly letting droplets shrink by permeation of water from the drops into the oil and also from the drops through the thin, polymer-based chip. Water permeation across the polymer foil decreases linearly with increasing foil thickness and decreased permeability of the material. In case of the 50 to 75 μm thick cyclic-olefin-copolymer (COC) sheets used here, the evaporative water loss amounted to a few percent per hour. When water evaporates from the drop, the solute concentrations inside the drop increase and hence the protein supersaturation also increases. As this corresponds to an increased nucleation rate, one would expect to yield a larger fraction of droplets with multiple crystals. We did not observe such an effect and attribute this to the fact that once the first crystal nucleates, its subsequent growth reduces the supersaturation of the solution enough to prevent another crystal from nucleating. We consistently achieved one crystal per drop, which argues for the robustness of the method. Once all droplets had nucleated crystals, we immersed the capillary/chip into an oil bath to prevent further evaporation. Alternatively we achieved equally good results with storing chips in a water bath to which a vial containing an oil reservoir was connected to the chip and all other inlets where sealed.

4. X-Ray Semi-Transparent Chip Fabrication

Figure 10:
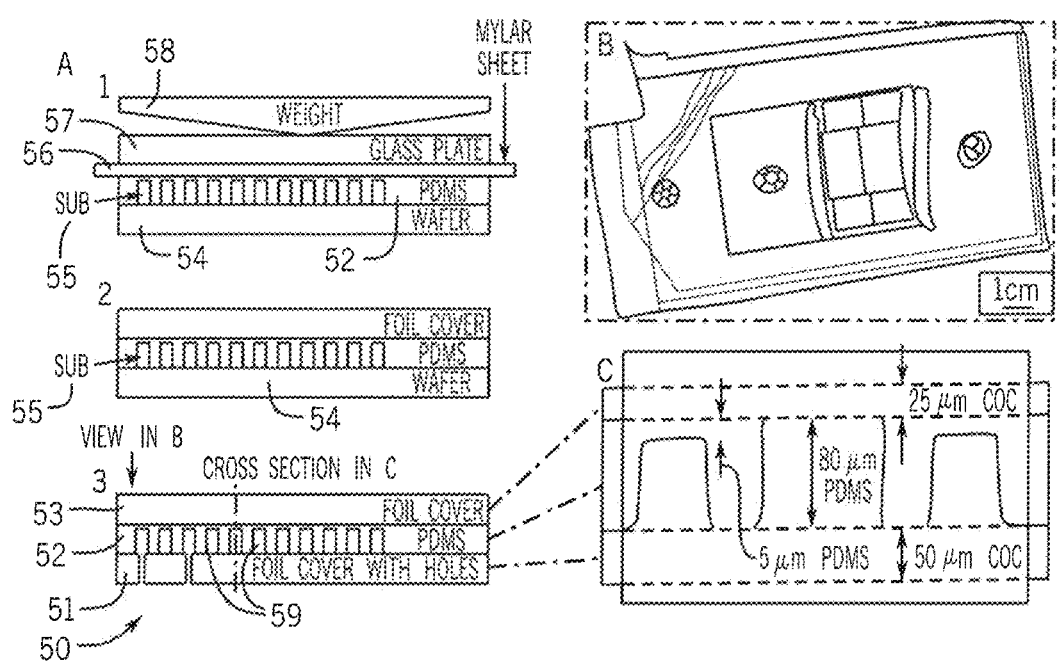
FIG. 10 shows X-ray chip fabrication according to the invention. In the transverse cross-sectional view of (A), poly(dimethylsiloxane) (PDMS) resin was squeezed into a thin layer onto the SU8-master. After curing, a foil cover was bonded onto the featured PDMS using a silane coupling-chemistry. Then the reinforced PDMS film was peeled off and the chip was lidded using another foil cover. In (B), top view and (C) cross-section of a device made from cyclic-olefin-copolymer (COC) foil covers and PDMS. A 5 mm thick slab of PDMS was bonded to the foil cover with the inlets to form a manifold (see B) for injecting the emulsion into the chip.
Figure 10D:
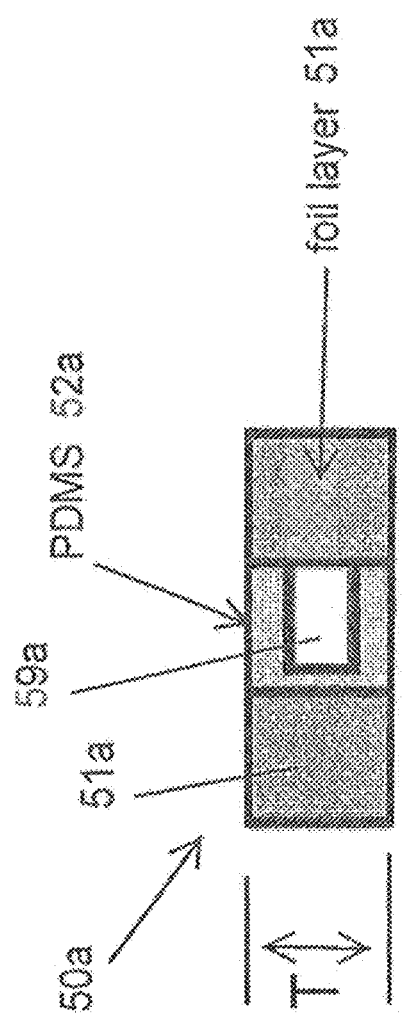
FIG. 10D shows a transverse partial cross-sectional view of a horizontally oriented single layer chip.

Looking at FIGS. 10 and 10D, chips 50 were sealed, which is colloquially referred to in the thermoplastic industry as 'lidding', by bonding cyclic-olefin-copolymer (COC)-foil or Kapton® polyimide-foil 51, 53 to both sides of the thin poly(dimethylsiloxane) (PDMS) slab 52 containing the channels 59 (FIG. 10A3). (The channels could also be as shown in FIGS. 3A to 3C.) PDMS (Sylgard® 184 from Dow Corning) with ratio 1:5 of curing agent to base was molded on a standard SU8-master 55 by squeezing the uncured PDMS resin into a thin film using a glass plate 57 and a weight 58. To facilitate release of the PDMS film, the master was surface treated with a fluorophilic coating by spin-coating 1:20 Cytop CTL-809M in CTsolv.100E (both Bellex International) onto the master. We then baked the wafer for 1 hour at 150° C. We placed a 30 μm thick Mylar foil 56 (DuPont) between PDMS 52 and glass 57 to allow for easy removal of the glass slide after PDMS curing. We pre-cured the PDMS for 4 hours at room temperature before we removed the weight and transferred the complete stack into the oven to drive the curing reaction to completion at 72° C. for another hour.

We either used COC (TOPAS® 5013 cyclic olefin linear olefin copolymer from Advanced Polymers) or Kapton® poly(4,4-oxydiphenylene pyromellitimide) (American Durafilm), depending on experimental requirements. COC is more brittle than Kapton®, but has a lower water vapor permeability. The thinnest commercial COC we used was 25 μm thin TOPAS®, while Kapton® as thin as 8 μm can be purchased as bulk foil. We chemically bonded either foil substrate 51, 53 to the featured PDMS 52 using a silane coupling chemistry. In brief, both foil and PDMS are activated in an oxygen plasma and then incubated for 25 minutes in an aqueous solution of a different silane each; 1 vol % of 3-aminopropyltrimethoxysilane (APTMS, 97% from Aldrich), and 1 vol % of 3-glycidoxypropyltrimethoxysilane (GPTMS, 98%, from Aldrich). The two silanes are such that they can form an epoxy bond when brought in contact. Upon removing foil and PDMS from the batch, we dried both with a stream of nitrogen gas and then carefully brought them in contact using tweezers to prevent trapping air bubbles between both layers. The chip 50 was then incubated in the oven at 72° C. for 1 hour to maximize chemical cross-linking. The process was repeated to lid the other side of the chip. Upon assembly, the chip 50 was surface treated with a fluorophilic coating to prevent protein interaction with the channel surface. For this, 1:20 Cytop CTX-109AE in CTsolv 100E (both Bellex International) was dead-end filled into the chip by plugging all outlets and slowly injecting the Cytop solution through the inlet into the chip. This causes gas bubbles trapped inside the chip to become pressurized which promotes the gas to dissolve into solution and also to permeate across the chip walls to result in a completely filled, bubble free device. The chip was then incubated at 90° C. for at least 12 hours to evaporate the solvent away and also to accelerate chemical cross-linking between fluoropolymer and chip surface.

In the non-limiting example of FIG. 10A(3), the foil cover 53 has a bottom to top thickness of about 25 μm, the PDMS layer 52 has a bottom to top thickness of about 80 μm with channels of a bottom to top height of about 75 μm, and the foil cover 51 with holes has a bottom to top thickness of about 50 μm. However, a horizontally oriented single layer chip 50a is also possible as shown in the non-limiting example of FIG. 10D in which the single layer of foil 51a has a bottom to top thickness T of about 25 μm. The PDMS storage section 52a with channels 59a is oriented vertically in the layer of foil 51a as shown in FIG. 10D. A plurality of storage sections can be oriented vertically in the layer of foil. The embodiment of FIG. 10D could provide for improved efficiency by reducing the time to optimize conditions for the largest crystal.

5. In-Situ Diffraction

Figure 11:
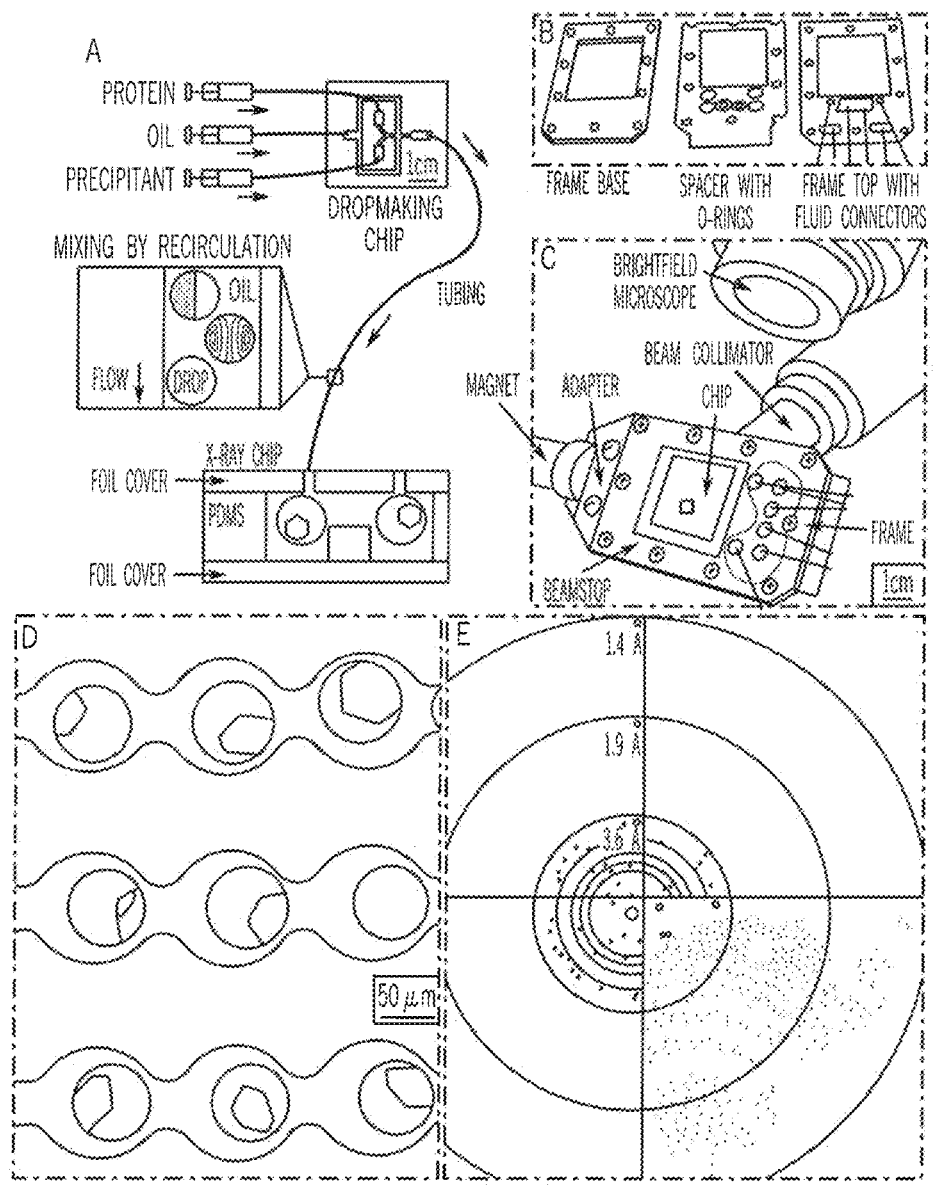
FIG. 11 shows: in (A), a monodisperse emulsion being prepared using a dedicated dropmaking chip as illustrated in FIG. 9(D) and directly routed into the chip for serial crystallography for storage. In (B), we used a laser-cut frame to hold and to port into the X-ray semi-transparent chip. In (C), there is shown an X-ray semi-transparent chip mounted on the goniometer inside the Cornell University CHESS F1 beamline. In (D), there is shown glucose isomerase crystals inside of the microfluidic device. Using a motorized stage, each crystal can be centered in the collimated X-ray beam. The beam is 100 µm in diameter. In (E), there is shown a representative diffraction pattern of a glucose isomerase crystal taken at room temperature from inside the chip. Crystals diffracted to 1.4 Å resolution with a mosaicity as low as 0.04°. The bottom right quadrant shows the diffraction pattern after background subtraction, using the Adxv diffraction pattern visualization tool with subtract background option.

We mounted the X-ray transparent chip into a custom acrylic frame to collect diffraction data (FIG. 11). The acrylic frame was cut to shape from 3 mm thick acrylic sheet using a 40 W $CO_2$ Hobby Laser cutter with a 1.5" focus lens (Full Spectrum Laser). To create ports into the foil-chip we drilled through holes into the acrylic frame with the laser cutter. Blunt needle pins (23 gauge) were then placed into the holes and glued into position with 5 minute epoxy. We connected #30 AWG poly(tetrafluoroethylene) (PTFE) tubing (Cole Palmer) to the pins using PDMS cubes with through holes punched into them using 0.75 mm Harrison Uni-Core biopsy punches (Ted Pella). Buna O-rings, 70 durometer, size 002 (McMaster Carr) were then used to seal the foil-chip to the hollow metal pins. For easy alignment the o-rings were fit into a 1 mm thick poly(ethyleneterephthalate) (PET) spacer that also was fabricated with the laser cutter. X-ray semi-transparent foil-chips were mounted into a frame for the duration of each experiment. Each frame was held together by 10 self-tapping 3/16" Pan Head 2-28 Phillips screws (McMaster Carr) to lock the chip into position and to minimize flow induced inside the chip from mechanically bending the thin foil chip. To mount the frame-chip assembly in the synchrotron we machined a stainless steel adapter that a frame could be mounted onto using two screws (FIG. 11B).

For the proof of principle experiment, we fabricated an X-ray semi-transparent chip with the "dropspot" geometry that can hold up to 8000 emulsion droplets in cavities with 150 μm diameter each (FIGS. 10 B&C). The fluorinated oil has a density of 2 g/mL, while the water drops have a density of 1 g/mL. Thus there is a strong tendency for the drops to float to the top of the oil, or "cream". Surface tension forces arrest droplets in a cavity and prevent them from creaming to one side of the chip. We produced a monodisperse ~110 μm diameter emulsion of 30 mg/ml glucose isomerase, 100 mM Ammonium Sulfate, pH 7.3, 20 wt % PEG 10 k MW final concentration in a standard dropmaker (FIG. 10D). Droplets exiting the dropmaker were immediately routed into the X-ray semi-transparent serial crystallography chip by simply plumbing the dropmaker outlet into the dropspot inlet (FIG. 11A). After the dropspot chip was loaded, we dead-end plugged its outlet except for one inlet where we kept HFE-7500 oil entering the chip using hydrostatic pressure to compensate for oil evaporation from the chip. We incubated the chip at room temperature for three days and monitored crystallization, before transferring into a water bath to prevent further evaporation. By then, most droplets had shrunken to about ~90 μm diameter and more than 90% of them had nucleated a single crystal. Crystals grew to about 50 μm by 40 μm by 30 μm in size at room temperature (~25° C.).

X-ray diffraction data were collected at Cornell High Energy Synchrotron Source (CHESS), beamline F1 ($\lambda$=0.9179 Å, E=13.508 keV), using a 100 μm monochromatic X-ray beam from a 24-pole wiggler. The chips were mounted at a distance of 200 mm from an Area Detector Systems Corporation (ADSC) Quantum 270 (Q270) detector, corresponding to a largest inscribed circle of resolution of 1.4 Å. The detector face was oriented perpendicular to the beam. For selected crystals within the chip, data sets were collected at room temperature (~25° C.). Each recorded data set comprised 10 frames, for a total of 10° oscillation. Each image consisted of a 5 second exposure with a 1° oscillation step size. A total of 1520 images were collected from 152 glucose isomerase crystals in three different dropspot chips.

6. X-Ray Structure Determination

The software HKL-2000 was used to index, refine, integrate and scale each 10° data set before merging. Parameters including unit-cell size, chi-squared values, resolution, mosaicity, and completeness were evaluated for every partial data set during the indexing and scaling process. From these partial data sets, with 1520 frames total, we selected 262 frames from 72 crystals by rejecting frames with a mosaic spread higher than 0.1° and chi-squared x and y (corresponding to discrepancy between observed and predicted spot positions) above 2. Some frames were later rejected because of poor scaling statistics; the final data set included 248 frames.

Glucose isomerase crystals were determined to have a space group of I222, and diffracted to an average of 2 Å; an example image is shown in FIG. 11E. In some crystals, diffraction extended to 1.4 Å, with a mosaic spread of 0.04.

The 248 selected frames were scaled together using Scalepack (HKL Research) and merged with Aimless. The limiting resolution of 2.09 Å was chosen as that at which CC1/2 dropped below 0.5. Statistics are given in Table 2. The merged data set covered 93% of reciprocal space, suggesting that preferred orientation of the crystals was not a major problem. The glucose isomerase structure was readily solved by molecular replacement with Molrep using the structure previously determined at 1.90 Å resolution (PDB ID: 8XIA), with waters removed. Prior to refinement, we randomly flagged 5% of the reflections for $R_{free}$ analysis.

Figure 12:
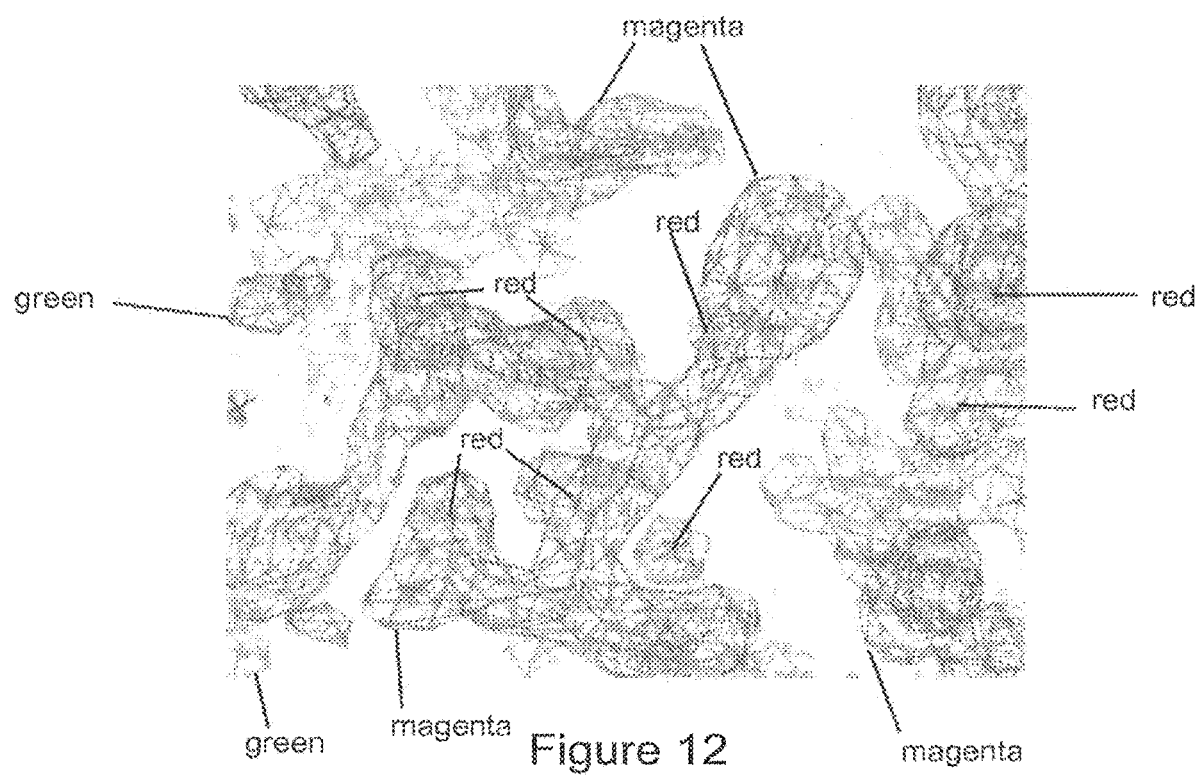
FIG. 12 shows part of the final refined structure showing the quality of the electron density map. 2Fo-Fc map is in magenta, contoured at 2 Å, Fo-Fc in red (negative) and green (positive), contoured at 3 Å.

Structure refinement was carried out through multiple iterations of Refmac, refining atomic coordinates and isotropic B-factors. 2Fo-Fc and Fo-Fc electron density maps were generated after each refinement step, and further refinement was carried out by manual inspection using Coot. In the refinement process, two disordered N-terminal residues were removed, as well as a bound sugar molecule present in the model but not in the crystal, and 124 water molecules were added. Final refinement gave R and $R_{free}$ of 14.4% and 17.5%, respectively. Complete processing statistics are given in Table 3. FIG. 12 shows the quality of the final refined structure.

TABLE 2

Processing results of merging the 248 frames obtained from 72 glucose isomerase crystals. Values in parentheses refer to the highest resolution bin (2.15-2.09 Å).

| | |
|---|---|
| Precipitant composition | 100 mM ammonium sulfate pH 7.0 + 20 wt % PEG 10,000 |
| Space Group | I222 |
| Unit-cell parameters (Å) | a = 93.94 b = 99.47, c = 102.85 |
| Resolution range (Å) | 49.7-2.09 (2.15-2.09) |
| No. of unique reflections | 26699 (2075) |
| Redundancy | 8.2 (8.1) |
| Completeness (%) | 93.2 (94) |
| $R_{merge}$ (%) | 0.191 (0.686) |
| $<I/\sigma (I)>$ | 7.8 (4.1) |
| Mosaicity (°) | 0.03-0.1 |

TABLE 3

Refinement and model statistics for glucose isomerase. Values in parentheses refer to the highest resolution bin.

| | |
|---|---|
| Resolution range (Å) | 49.7-2.09 (2.14-2.09) |
| Reflections used: working, total | 25395, 26685 (1879, 1974) |
| Completeness (%) | 92.4 (93.6) |
| R(working)/$R_{free}$ | 0.144/0.174 (0.186/0.227) |
| RMSD, bond lengths (Å) | 0.019 |
| RMSD, bond angles (°) | 1.93 |
| No. of protein/other atoms (non-hydrogen) | 3034/126 |
| Mean B value, all atoms (Å$^2$) | 17.6 |
| Ramachandran statistics (%); favored, allowed, outliers | 97.13, 2.35, 0.52 |

R and $R_{free}$ are calculated using $\Sigma|Fo| - |Fc|/\Sigma|Fo|$ for the working and free-set reflections, respectively

7. Conclusion

In this example, we present a technology that optimizes the kinetics of crystallization, eliminates crystal handling, eliminates cryoprotection and simplifies collection of diffraction data for structural biology. In this example, we developed processing methods for protein crystallization that follow the ideal kinetic pathway of slowly increasing supersaturation until a single crystal nucleates and then reducing supersaturation so that one crystal grows slowly to allow annealing of defects. Sample volume is not a thermodynamic variable in phase equilibrium, but since crystallization is a non-equilibrium process, volume plays a key role in determining the kinetics of crystallization. We believe using a combination of simulation, theory and experiment that selecting the appropriate droplet diameter, w, guarantees that only one crystal per drop will form when the drop volume $V<\sim(D/J)^{d/2+d}$. We identify the critical drop diameter for a particular crystallization condition in a single experiment by using a polydisperse emulsion with droplets ranging from a few micrometers to a few hundreds of micrometers in size. These polydisperse emulsions can be made with ease within seconds using only a pipette and a test tube. The probability of crystallization is proportional to drop volume. As we use drops of order 1 nanoliter, which are smaller drops than employed by other methods, the nucleation rates and supersaturation that we use are higher than usual.

Employing these kinetic processing methods, we grew monodisperse crystals compartmentalized in emulsion droplets, with one crystal per drop. Monodisperse, microfluidically produced drops of supersaturated protein solutions were stored on chip and slowly concentrated as water permeated through the thin foil chip. Single crystals per drop were nucleated and grown on-chip in identical conditions. While cyro-cooled crystals can be stored almost indefinitely, the crystals grown and stored in our chips are stable for several weeks when the chips are stored in a water bath connected to an oil reservoir, which prevents evaporation and hence drying out. The chip for nucleating crystals was thin enough to be X-ray semi-transparent and diffraction patterns were collected from these crystals on-chip at room temperature. The structure of glucose isomerase was solved and refined at 2.09 Å resolution, to an $R_{cryst}/R_{free}$ of 0.144/0.174, using merged diffraction datasets from 72 crystals of about 50 μm by 40 μm by 30 μm in size.

Diffraction from room temperature crystals stored on the chip in which they were nucleated and grown has many advantages over traditional off-chip cyroprotected crystals. On-chip diffraction means the crystals are not removed from their mother liquor, which can lead to dehydration and osmotic shock of the crystals and the generation of stress and strain. Room temperature diffraction eliminates the laborious step of cryoprotection and has the additional effect of lowering the mosaicity as cryoprotection generates stresses due to changing solvent conditions and temperature induced volume changes. Our chip can be inexpensively mass produced and is simple to operate without the need of controlling valves. We envision a chip that uses temperature and concentration gradients to discover optimal crystal growth conditions wherein crystals would be grown at the optimal conditions to create a stream of tiny crystals that would be serially conveyed to a part of the chip with ultra thin windows for in-situ diffraction.

Example 4

In this example, we illustrate fabrication of an X-ray transparent crystallization device.

Harvesting crystals from microfluidic devices damages crystals, because stresses introduced by environmental changes and mechanical manipulation can strain or destroy protein crystals. We seek to overcome this limitation by leaving the crystals on the chip, bathed In the mother liquor from which the crystals were produced. We do this by making the chips so thin that x-rays pass through the chip without significant scatter. We use tooling to produce thin foil microfluidic devices. This enables us to produce thinner chips.

A microfluidic device of this example greatly improves the determination of protein structure, which is necessary for fundamental knowledge, medical research and pharmaceutics. The chip produces crystals using novel crystallization optimization protocols. Reducing the chip in size to 150 microns will render it x-ray transparent, permitting structures to be obtained from crystals on chip. The non-limiting example crystal chip has two integrated layers, one containing protein and the other buffer solutions, linked by a selective membrane. Current technologies requires crystals to be harvested manually, damaging the fragile crystals. To manufacture the thin crystal chip, we use a thermo-press for embossing the microfluidics into biocompatible plastic films.

The microfabrication tooling includes a laminator and a thermal press that operates in the 1 to 10 psi pressure ranges. The custom tooling includes a pressure sensor, piston system, temperature regulator (up to 300° C.), and a vacuum pump. The tool may be configurable to work in two different ways. First, actuated by pressurized air, two heated metal plates can be pressed against each other to produce thin plastic plaques and foils. Second, a vented chamber can be sandwiched between the heated plates to pull and press a thin foil onto an embossing master using the vacuum.

An example sequence of steps for manufacturing an X-ray transparent crystallization device is as follows. Step 1 comprises manufacturing a master, i.e. by micromilling a master form. Step 2 comprises casting a negative mold insert with PDMS on the micromilled master form. Step 3 comprises assembling the negative mold insert and a polymer (e.g., COC) foil into an aluminum tool holder prior to evacuation. Step 4 comprises tightly sealing the tool holder and heating above a glass transition temperature of the polymer foil. Step 5 comprises the application of pressurized nitrogen into the interior of the tool holder. Step 6 comprises demolding the polymer foil after cooling.

A first negative mold insert can be created for embossing a microfluidic channel having a plurality of microwells in a first polymer foil. A second negative mold insert can be created for embossing one or more reservoirs in a second polymer foil. A fastening system can be used for attaching the first polymer foil to a first side of a dialysis membrane and for attaching the second polymer foil to a second opposite side of the dialysis membrane creating a structure as in FIG. 10(A)3.

Example 5

In this example, we illustrate X-ray transparent differential permeation chips. FIG. 13 shows cross sectional views of an example single membrane differential permeation X-ray chip 60 and an example double membrane differential permeation X-ray chip 70 according to the invention. The concept is to make the membrane have a wedge-shape cross-section to generate a gradient of permeation flux. The non-limiting example membranes in FIG. 13 use a permeation membrane attached to the X-ray chip in a reversible way so that the differential permeation membrane can be removed before shooting crystals. The devices of FIG. 13 operate by dipping the assembly into different reservoir solutions, i.e., first into a high salt buffer, or exposed to air to shrink drops and then into water to swell drops. The double membrane differential permeation X-ray chip has the permeation control on both sides for a two times transfer rate. The differential permeation membrane could use an elastomeric (e.g., PDMS) membrane, to only permeate water and non-polar solutes.

In the single membrane differential permeation X-ray chip 60 of FIG. 13, cyclic-olefin-copolymer (COC)-foil or Kapton® polyimide-foils 61, 63 are bonded to both sides of a poly(dimethylsiloxane) (PDMS) layer 62 containing the channels 69. Fluid ports 67 are in fluid communication with the channels 69. A permeation barrier 64 is bonded to the foil 62. A differential permeation membrane 65 of varying thickness creating a wedge-shape cross-section is bonded to the foil 61. The membrane 65 may comprise a dialysis membrane, or the membrane 65 may comprise a membrane permeable to water, or the membrane 65 may comprise a polyethersulfone, or the membrane 65 may comprise regenerated cellulose or cellulose ester. The membrane 65 may be hydrophilic. The foils 61, 63 may have a thickness of about 5 µm to about 100 µm, the PDMS layer 62 may have a bottom to top thickness of about 50 µm to about 150 µm with channels of a bottom to top height of about 45 µm to about 145 µm, and the membrane 65 may have a thickness varying from about 5 µm to about 100 µm.

In the double membrane differential permeation X-ray chip 70 of FIG. 13, cyclic-olefin-copolymer (COC)-foil or Kapton® polyimide-foils 71, 73 are bonded to both sides of a poly(dimethylsiloxane) (PDMS) layer 72 containing the channels 79. Fluid ports 77 are in fluid communication with the channels 79. Differential permeation membranes 75, 76 of varying thickness creating a wedge-shape cross-section are bonded to the foils 71, 73. The membranes 75, 76 may comprise a dialysis membrane, or the membranes 75, 76 may comprise a membrane permeable to water, or the membranes 75, 76 may comprise a polyethersulfone, or the membranes 75, 76 may comprise regenerated cellulose or cellulose ester. The membranes 75, 76 may be hydrophilic. The foils 71, 73 may have a thickness of about 5 µm to about 100 µm, the PDMS layer 72 may have a bottom to top thickness of about 50 µm to about 150 µm with channels of a bottom to top height of about 45 µm to about 145 µm, and the membranes 75, 76 may have a thickness varying from about 5 µm to about 100 µm.

Example 6

Figure 14:
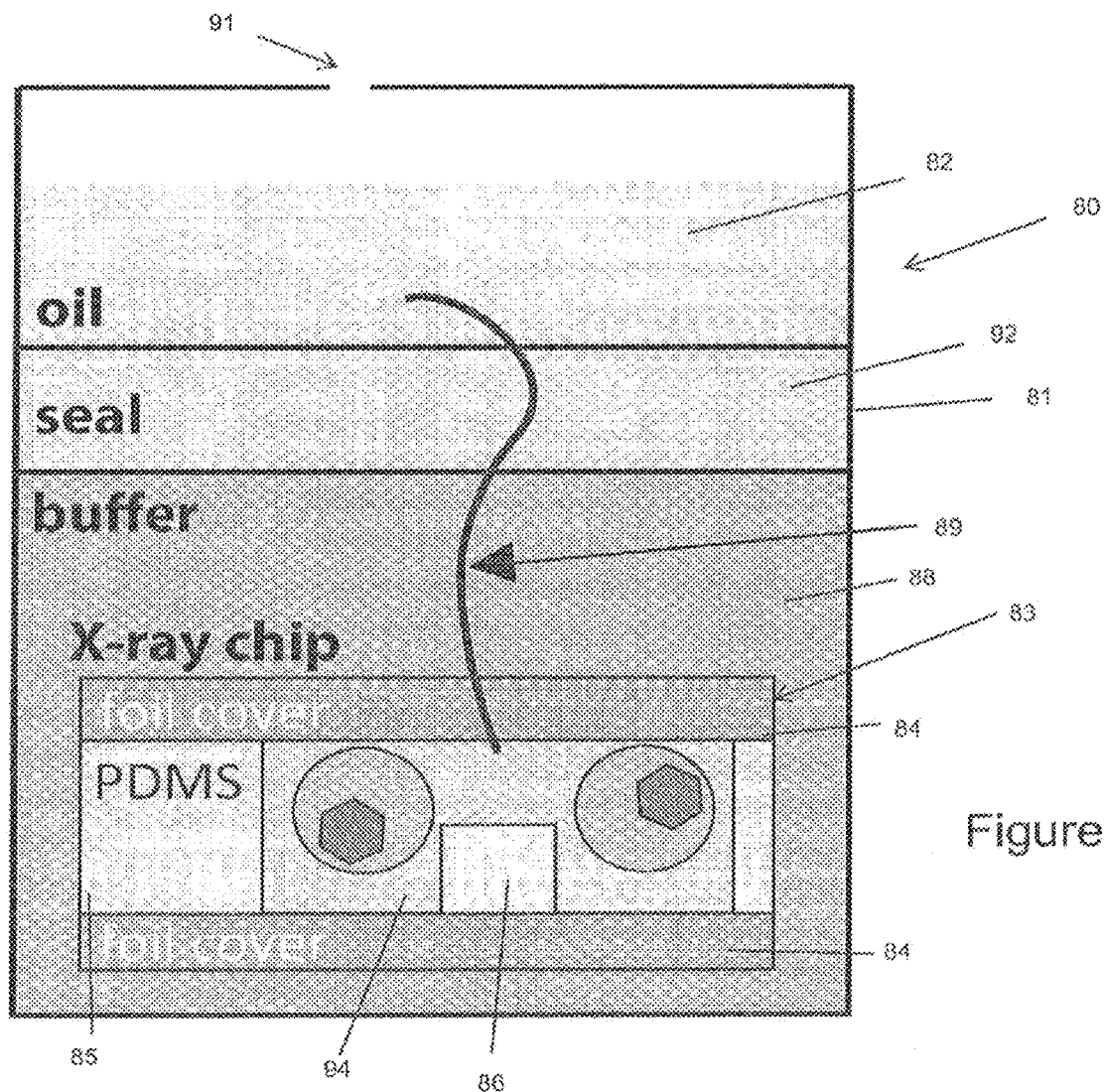
FIG. 14 shows a cross sectional view of an X-ray chip storage container according to the invention.

In this example, we illustrate an X-ray transparent chip storage container. Referring to FIG. 14, there is shown a cross sectional view of an X-ray chip storage container 80 according to the invention. The storage container prevents both: uncontrolled loss of oil and buffer. FIG. 14 shows an all in one vial 81, but it can be separate vials as well. Using thin X-ray transparent foils comes at the expense of the chip being sensitive to drying out over a few hours and hence long-term storage is a concern. We use a special vial 81 as shown in FIG. 14 to be able to transport (such as by mail) loaded chips.

The components include a vial 82 of oil connected to the X-ray chip 83, with all other chip fluid outlets being blocked. The vial 82 has an opening 91 such that hydrostatic pressure can push fresh oil into the chip to replace oil that has evaporated. The opening 91 can be sealed during shipment and opened (such as by breaking a frangible seal) before use. The chip 83 has cyclic-olefin-copolymer (COC)-foil or Kapton® polyimide-foils 84 bonded to both sides of a poly(dimethylsiloxane) (PDMS) layer 85 containing channels 86. The chip 83 itself is placed in an aqueous bath 88 of buffer to prevent water evaporation. Fluid conduit 89 is in fluid communication with a reservoir 94 of the layer 85 and the vial 82 of oil to allow transfer of the oil by way of hydrostatic pressure. Taking these measures extends the shelf life to at least a month for an X-ray chip.

Example 7

In this example, we illustrate an apparatus for controlling a reaction or a phase transition in which hydrostatic pressure driven flow is used to control dialysis. Non-limiting examples of the reaction are one or more of the following: steady-state and self-assembly reactions at or far from equilibrium; perturbation analysis of reaction networks; cell synchronization; cell and tissue differentiation; and/or chemostat reactions with cells and cell populations. Non-limiting examples of the phase transition are one or more of the following: crystallization and co-crystallization of small molecules, biological macromolecules, colloids and combinations thereof; liquid crystal phase transitions; gelation; liquid-liquid separation; protein folding; and/or DNA melting or condensation.

Figure 15:
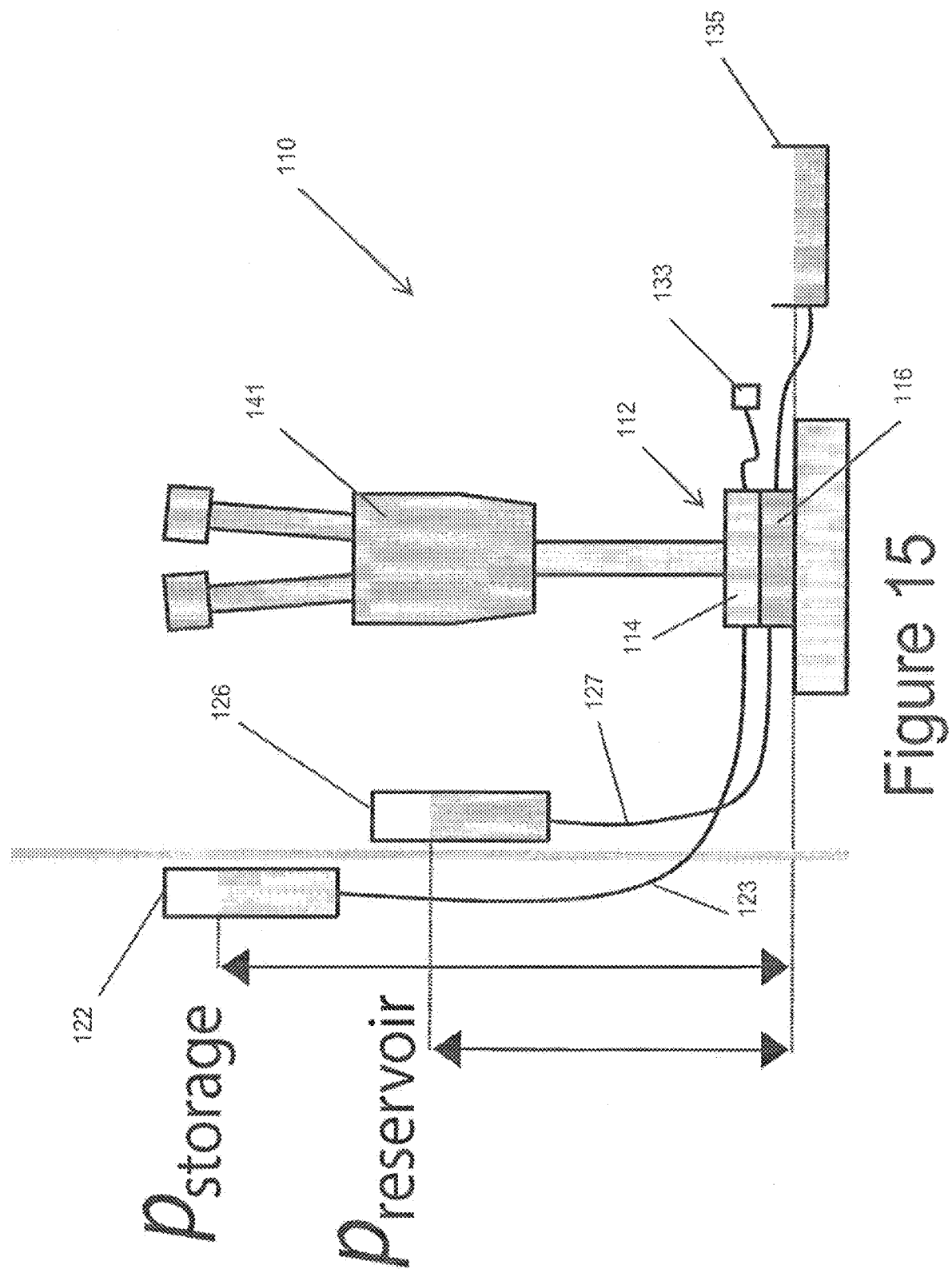
FIG. 15 shows a schematic of a hydrostatic pressure driven flow system for controlling dialysis in an X-ray chip according to the invention.

Looking at FIG. 15, the non-limiting example apparatus 110 for controlling a reaction or a phase transition includes a microfluidic device 112 such as that shown in FIG. 1. In FIG. 15, only the storage layer 114 and the reservoir layer 116 of the microfluidic device 112 are shown for ease of illustration. The microfluidic device 112 of the apparatus 110 includes a reservoir layer defining a reservoir; a dialysis membrane disposed on the reservoir layer; a wetting control layer disposed on the membrane; and a storage layer disposed on the wetting control layer. The wetting control layer and the storage layer define a microfluidic channel comprising an upstream portion, a downstream portion, a first fluid path in fluid communication with the upstream portion and the downstream portion, and a storage well positioned within the first fluid path. The wetting control layer includes a fluid passageway in fluid communication with the storage well and the membrane. The wetting control layer is capable of wetting a first fluid introduced into the microfluidic channel, the first fluid comprising a hydrophilic, lipophilic, fluorophilic or gas phase as the continuous phase in the microfluidic channel.

The apparatus 110 also includes a source of oil, vial 122, in fluid communication via a conduit 123 with the microfluidic channel of the microfluidic device 112; and a source of an aqueous fluid, vial 126, in fluid communication via a conduit 127 with the reservoir of the microfluidic device 112. The vials 122, 126 containing the oil and buffer have open tops such that hydrostatic pressure regulates transport fluxes across the membrane of the microfluidic device 112. Note pressures Pstorage and Preservoir in FIG. 15. Alternatively, a pressure controller can regulate transport fluxes across the membrane. Storage outlets 133 of the microfluidic channel can be blocked, and an outlet vessel 135 of the reservoir can be open. A microscope 141 is used for monitoring the reaction or the phase transition in the microfluidic device 112.

Example 8

Growth kinetics, the relationship between cell growth rate and nutrient supply, plays a vital role in the understanding of cell function. A chemostat is one example device for the study of the growth kinetics of microorganisms. Chemostats can maintain a constant population of a microorganism in a state of active growth. This may be done by periodically substituting a fraction of a culture with an equal volume of fresh, sterile, chemically defined growth medium. However, one major difficulty with a chemostat is the need to continuously supply medium as continuous cultures can run for days or weeks at steady state.

A microfluidic chemostat of the present invention offers a way to address the difficulties relating to conventional continuous culture systems. A microfluidic chemostat of the present invention can run for long periods of time consuming much less media.

Figure 16:
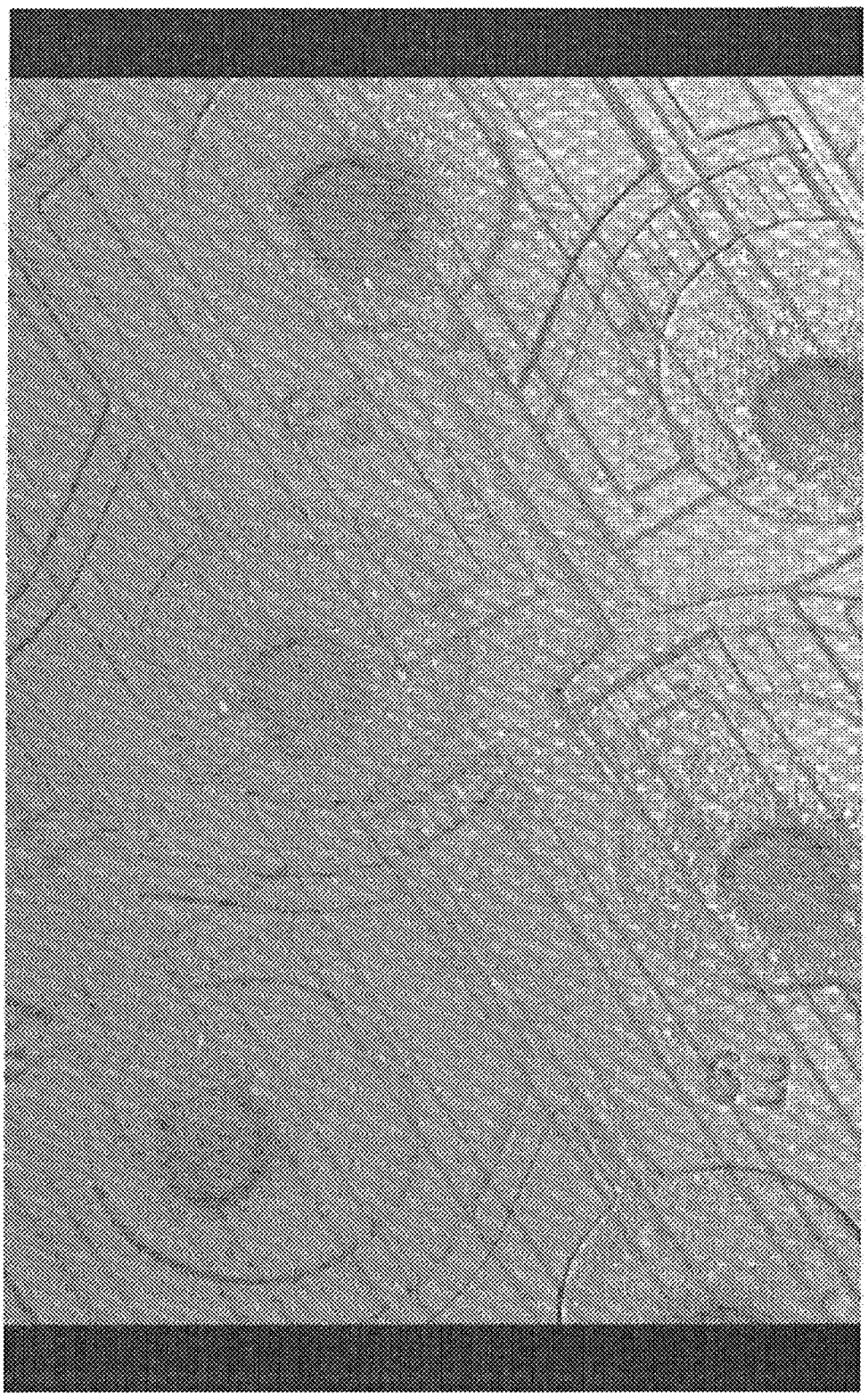
FIG. 16 shows yeast populations in wells having a volume of 20 nanoliters each at a time lapse of approximately one week in a dialysis chip according to the invention.

We prepared a dialysis chip as in Example 1 with the microfluidic channels 40 of FIG. 3. This dialysis chip can be used for studying the biome. We used this dialysis chip with microfluidic channels 40 as a chemostat that kept alive yeast populations for a week. The device operated at constant conditions—continuously supplying nutrients and removing waste and yeast, thereby maintaining a constant population. FIG. 16 shows yeast populations in wells having a volume of 20 nanoliters each at a time lapse of approximately one week.

Thus, the invention provides microfluidic devices for investigating crystallization, and microfluidic devices for controlling a reaction or a phase transition.

Although the invention has been described in considerable detail with reference to certain embodiments, one skilled in the art will appreciate that the present invention can be practiced by other than the described embodiments, which have been presented for purposes of illustration and not of limitation. Therefore, the scope of the appended claims should not be limited to the description of the embodiments contained herein.

What is claimed is:

1. A device for supporting crystals in an X-ray diffraction apparatus, the device comprising:
    a first X-ray transparent layer having a microwell formed therein;
    a second X-ray transparent layer including a reservoir; and
    a membrane,
    wherein the first X-ray transparent layer is attached to a first side of a membrane,
    wherein the second X-ray transparent layer is attached to a second opposite side of the membrane, and
    wherein at least a portion of an opening of the microwell and at least a portion of an opening of the reservoir are in fluid communication, via the membrane, and
    wherein the membrane facilitates at least one of exchange of small molecule solutes, exchange of salt, permeation of water, or permeation of non-polar solutes between the microwell and the reservoir.

2. The device of claim 1 wherein:
    a plurality of microwells are positioned within the first X-ray transparent layer,
    the second X-ray transparent layer defines a plurality of reservoirs, and
    each reservoir is aligned with one of the microwells.

3. The device of claim 1 wherein:
    the first X-ray transparent layer comprises an X-ray transparent material selected from the group consisting of cycloolefin polymers, cycloolefin copolymers, polyimides, graphene, and silicon nitride, and
    the second X-ray transparent layer comprises the X-ray transparent material.

4. The device of claim 1, wherein the membrane is selected from the group consisting of a dialysis membrane, and an elastomeric membrane.

5. The device of claim 4 wherein:
    the first X-ray transparent layer is less than 200 microns in thickness;
    the second X-ray transparent layer is less than 200 microns in thickness; and
    the membrane is less than 50 microns in thickness.

6. A device for supporting crystals in an X-ray diffraction apparatus, the device comprising:
    a storage layer including a microwell positioned therein;
    a first X-ray transparent layer attached to a first side of the storage layer;
    a second X-ray transparent layer attached to a second opposite side of the storage layer; and
    a fluid port, the fluid port being in communication with the microwell, and the fluid port is in the first X-ray transparent layer.

7. The device of claim 6, wherein the storage layer includes a microfluidic channel.

8. The device of claim 6, wherein the storage layer includes a plurality of microwells positioned therein for containing the crystals.

9. The device of claim 8, further comprising a plurality of fluid ports, the plurality of fluid ports including the fluid port; and
    wherein each fluid port within the plurality of fluid ports is in communication with a corresponding microwell within the plurality of microwells.

10. The device of claim 9, wherein the plurality of fluid ports are in the first X-ray transparent layer.

11. The device of claim 8, further comprising a differential permeation membrane attached to the first X-ray transparent layer.

12. The device of claim 6, further comprising a permeation barrier attached to the second X-ray transparent layer.

13. The device of claim 11, wherein the differential permeation membrane is removably attached to the first X-ray transparent layer.

14. The device of claim 11, wherein the differential permeation membrane has a thickness that varies from a first end of the differential permeation membrane to an opposite second end of the differential permeation membrane.

15. The device of claim 11, wherein the differential permeation membrane is wedge-shaped in cross-section.

16. The device of claim 6, further comprising a second differential permeation membrane attached to the second X-ray transparent layer.

17. The device of claim 16, wherein the second differential permeation membrane has a thickness that varies from a first end of the second differential permeation membrane to an opposite second end of the second differential permeation membrane.

18. The device of claim 16, wherein the second differential permeation membrane is wedge-shaped in cross-section.

19. The device of claim 6, further comprising:
    a vial dimensioned to receive the device, the vial defining an internal volume therein, the vial comprising:
        an opening through a wall of the vial;
        an aqueous fluid disposed within the internal volume;
        a seal positioned above the aqueous fluid and disposed within the internal volume;
        a source of oil disposed above the seal and within the internal volume; and
        a conduit in fluid communication with the source of oil at a first end of the conduit; and wherein, when the device is placed into the aqueous fluid, a second end of the conduit is configured to be received into a reservoir within the storage layer, such that a hydrostatic pressure of the source of oil transfers oil into the reservoir.

20. A method for acquiring X-ray diffraction images of crystals, the method comprising:
(a) microfluidically producing droplets;
(b) feeding the droplets into a microwell of an X-ray device, via a microfluidic channel in fluid communication with the microwell, the X-ray device being at least partially X-ray transparent;
(c) nucleating and growing a crystal in least some of the droplets to create a plurality of crystals; and
(d) obtaining an X-ray diffraction pattern from the plurality of crystals.

21. The method of claim 20, wherein the droplets are monodisperse.

22. The method of claim 21, wherein the droplets have a size such that a single crystal is grown in each droplet.

23. The method of claim 20, wherein each crystal grows by permeation of water in the X-ray device.

24. The method of claim 20, wherein each crystal grows by dialysis in the X-ray device.

25. The method of claim 20, wherein the method does not include a cryoprotection step.

26. The method of claim 20, wherein the X-ray device has a second microwell in fluid communication within a second microfluidic channel, the method further comprising feeding the droplets into the second microwell, via the second microfluidic channel.

* * * * *

UNITED STATES PATENT AND TRADEMARK OFFICE
CERTIFICATE OF CORRECTION

PATENT NO. : 10,942,095 B2
APPLICATION NO. : 16/447369
DATED : March 9, 2021
INVENTOR(S) : Seth Fraden et al.

Page 1 of 1

It is certified that error appears in the above-identified patent and that said Letters Patent is hereby corrected as shown below:

In the Specification

Column 4, Line 33, "$(x(t))= x-(1-e^{-kt})$" should be --$(x(t))= x_\infty(1-e^{-kt})$--.

Column 4, Line 38, "$x-$" should be --$x_\infty$--.

Column 4, Line 39, "$x-=V=w^d$" should be --$x_\infty=V=w^d$--.

Column 4, Line 42, "$x-$" should be --$x_\infty$--.

Column 4, Line 43, "$w^d=V/x\infty$" should be --$w^d=V/x_\infty$--.

Column 16, Line 31, "Zonyle" should be --Zonyl®--.

Column 18, Lines 29-30, "SON ICC" should be --SONICC--.

Column 27, Line 24, "h tan" should be --than--.

Column 38, Line 55, "Pstorage and Preservoir" should be --$p_{storage}$ and $p_{reservoir}$--.

Signed and Sealed this
Fourth Day of May, 2021

Drew Hirshfeld
*Performing the Functions and Duties of the*
*Under Secretary of Commerce for Intellectual Property and*
*Director of the United States Patent and Trademark Office*